United States Patent
Kakuda et al.

(10) Patent No.: US 6,271,259 B1
(45) Date of Patent: *Aug. 7, 2001

(54) METHOD FOR IMPROVING THE BRAIN FUNCTION, INHIBITING GLUTAMATE EXCITOTOXICITY AND RESCUING FROM NEURONAL DEATH

(75) Inventors: Takami Kakuda; Ayumu Nozawa; Takanobu Takihara; Iwao Sakane, all of Haibara-gun; Yoichiro Kuroda, Musashino; Kazuo Kobayashi, Tokyo; Masahiro Kawahara, Kokubunji; Akihiro Mizutani, Tachikawa; Kazuyo Muramoto, Kokubunji; Kunihiko Umezawa, Kesennuma, all of (JP)

(73) Assignee: Ito En, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/646,066

(22) Filed: May 7, 1996

(51) Int. Cl.⁷ .......................... A01H 37/12; A01H 37/44
(52) U.S. Cl. ............................................................ 514/563
(58) Field of Search ............................................ 514/563

(56) References Cited

FOREIGN PATENT DOCUMENTS 2-256656   10/1990   (JP) .
4-247033   9/1992    (JP) .

OTHER PUBLICATIONS

HCAPLUS abstract AN: 1995: 808365 (1995) Norin KK (JP 7173059).*

WPIDS abstract AN: 96–205436 [21] (1996) Itoen KK (JP 8073350).*

WPIDS abstract AN: 93–339641 [43] (1993) Kato, K et al. (JP 5246866).*

Medline abstract, AN 91165613, Mattson, M.P., 1990.*

JP 7173059 A2, Kawagishi et al. (English translation thereof), Jul. 1995.*

* cited by examiner

Primary Examiner—Theodore J. Criares
(74) Attorney, Agent, or Firm—McDermott, Will & Emery

(57) ABSTRACT

This invention is characterized by a brain function improving preparation containing theanine not less than 50 $\mu$M. It was confirmed that theanine could increase intracellular $Ca^{2+}$ concentration by acting on NMDA receptors even at a low dose of about 50 $\mu$M. Thus, the brain function improving preparation of this invention was shown to be capable of causing plastic change in neurons or neural circuit. Since theanine has been approved as a food additive and being consumed daily, its safety has no problem. Moreover, theanine passes the blood-brain barrier relatively easily and, thus, it is effective as an oral preparation.

10 Claims, 27 Drawing Sheets

METHOD FOR IMPROVING THE BRAIN FUNCTION, INHIBITING GLUTAMATE EXCITOTOXICITY AND RESCUING FROM NEURONAL DEATH

BACKGROUND OF THE INVENTION

1. Field of the Invention

This invention concerns the method for improving the brain function effective for treatment, improvement and prevention of brain metabolic or functional disorders including memory, learning and reflex reaction, symptoms such as Alzheimer's disease, Parkinson's disease and senile dementia associated pathophysiologically with the above disorders, as well as traumatic nervous disorder. The invention also concerns the method for inhibiting glutamate excitotoxicity and rescuing from neuronal death effective for treatment and prevention of glutamic acid-induced brain disorders, e.g. brain apoplexy including brain infarction and hemorrhage, and cerebral ischemia accompanying brain surgery and brain damage.

2. Description of the Prior Art

With the increase in senile population, the number of patients with partial damage in the brain such as senile dementia including Alzheimer's disease and with brain metabolic or functional disorders is increasing.

Various drugs including calcium hopantenate, sodium ozagrel, nilvadipine and anilacetaum have been approved as the brain function improving drugs, which are expected to accelerate brain function in these patients, or to prevent further progress in brain function disroders. Recently, tacrine, an anti-dementia agent, approved in USA has drawn attention.

It is also a known fact that repeated rehabilitation in the patients with partial brain damages results in reconstruction of neural circuit among the remaining neurons and, thus, recovering the brain function.

However, the conventional brain function improving drugs have the problem of causing some adverse reactions. Also, in case of rehabilitation which is not associated with the risk of adverse reaction, it is a trouble to consume a long duration and a great number of training sessions before recovery.

Now, glutamic acid receptors are the most popular receptors present in the brain and their deep association with brain functions such as memory and learning has been known.

The glutamic acid receptors are largely divided into N-methyl-D-aspartic acid (NMDA) receptors and non-NMDA receptors and the effects on NMDA receptors, in particular, are known as an essential factor in the long-term potentiation phenomenon which is a plastic change in the neurons and neural circuit. Moreover, increase in synaptic plasticity including the long-term potentiation is considered essential for fixation of memory and learning and, in fact, there has been a report stating that learning efficiency increased in the long-term potentiated rats. Further, it has been known that the increase in synaptic plasticity including the long-term potentiation is induced by an increase in $Ca^{2+}$ concentration in the neurons.

Meanwhile, glutamic acid, although it is associated with memory and learning as an excitable nerve transmitter by affecting glutamic acid receptors, has been known to cause excess excitation of neurons and exhibit neurotoxicity if it is present in excess. For example, it is known that excessive release of glutamic acid accompanying brain embolus or hemorrhage results in successive death of the surrounding neurons by its toxicity.

As glutamic acid antagonists which can alleviate glutamate excitotoxicity, inventions wherein a substance extracted from a spider toxin (Japanese Patent Publication No. 7(1995)-94419, etc.) or a new polyamine compound (Japanese Patent Publication No. 2(1990)-256656, etc.) are used as glutamic acid blockers have been published. Also, an invention utilizing selenite and selenite salts as glutamic acid antagonists has been published (Japanese Patent Publication No. 4(1992)-247033).

SUMMARY OF THE INVENTION

The inventors carried forward a study in earnest to offer a method for improving brain function not accompanied by adverse reactions such as shown by the conventional brain function improving agents. During the study, naturally existing substances consumed daily and having no immunological problem as well as being capable of increasing $Ca^{2+}$ concentration in neurons by acting on NMDA receptors were examined from various angles. Thus, by finding substances having the above effects, the inventors attempted to offer a method which would potentiate synaptic plasticity including long-potentiation, fix memory and learning, accelerate brain function recovery or prevent further advancement of brain dysfunction.

Then, the inventors finally found that theanine, an amine derivative typically contained in tea, possessed the said effects as well as inhibitory effect on glutamate excitotoxicity leading to completion of the invention.

In other words, this invention is characterized by the method wherein the brain function is improved by the effect of theanine on the brain neurons through the blood-brain barrier and, thus, increasing $Ca^{2+}$ concentration in the neurons without inducing adverse reactions and wherein glutamate excitotoxicity is inhibited by the effect of theanine on the neurons with excessive glutamic acid release.

BRIEF DESCRIPTION OF THE DRAWINGS

FIG. 5 shows the relative powers of δ-, θ-, α1- and β-waves in the cerebral cortex at 15 minutes after theanine adminstration at the respective doses.

FIG. 6 shows the relative powers of δ-, θ-, α1- and β-waves in the hippocampus at 15 minutes after theanine adminstration at the respective doses.

FIG. 7 shows the relative powers of δ-, θ-, α1- and β-waves in the amygdala at 15 minutes after theanine adminstration at the respective doses.

FIG. 8 shows the relative powers of δ-, θ-, α1-, α2- and β-waves in the cerebral cortex at 30 minutes after theanine administration at the respective doses.

FIG. 9 shows the relative powers of δ-, θ-, α1-, α2- and β-waves in the hippocampus at 30 minutes after theanine administration at the respective doses.

FIG. 10 shows the relative powers of δ-, θ-, α1-, α2- and β-waves in the amygdala at 30 minutes after theanine administration at the respective doses.

FIG. 11 shows the relative powers of δ-, θ-, α1-, α2- and β-waves in the cerebral cortex at 60 minutes after theanine administration at the respective doses.

FIG. 12 shows the relative powers of δ-, θ-, α1-, α2- and β-waves in the hippocampus at 60 minutes after theanine administration at the respective doses.

FIG. 13 shows the relative powers of δ-, θ-, α1-, α2- and β-waves in the amygdala at 60 minutes after theanine administration at the respective doses.

FIG. 14 shows the time-series change of the relative powers of δ-wave in the cerebral cortex, hippocampus and amygdala in 1 μmol theanine administration.

FIG. 15 shows the time-series change of the relative powers of θ-wave in the cerebral cortex, hippocampus and amygdala in 1 μmol theanine administration.

FIG. 16 shows the time-series change of the relative powers of α1-wave in the cerebral cortex, hippocampus and amygdala in 1 μmol theanine administration.

FIG. 17 shows the time-series change of the relative powers of α2-wave in the cerebral cortex, hippocampus and amygdala in 1 μmol theanine administration.

FIG. 18 shows the time-series change of the relative powers of β-wave in the cerebral cortex, hippocampus and amygdala in 1 μmol theanine administration.

FIG. 19 shows the time-series change of the relative powers of δ-wave in the cerebral cortex, hippocampus and amygdala in 2 μmol theanine administration.

FIG. 20 shows the time-series change of the relative powers of θ-wave in the cerebral cortex, hippocampus and amygdala in 2 μmol theanine administration.

FIG. 21 shows the time-series change of the relative powers of α1-wave in the cerebral cortex, hippocampus and amygdala in 2 μmol theanine administration.

FIG. 22 shows the time-series change of the relative powers of α2-wave in the cerebral cortex, hippocampus and amygdala in 2 μmol theanine administration.

FIG. 23 shows the time-series change of the relative powers of β-wave in the cerebral cortex, hippocampus and amygdala in 2 μmol theanine administration.

DETAILED DESCRIPTION OF THE INVENTION

Figure 1:
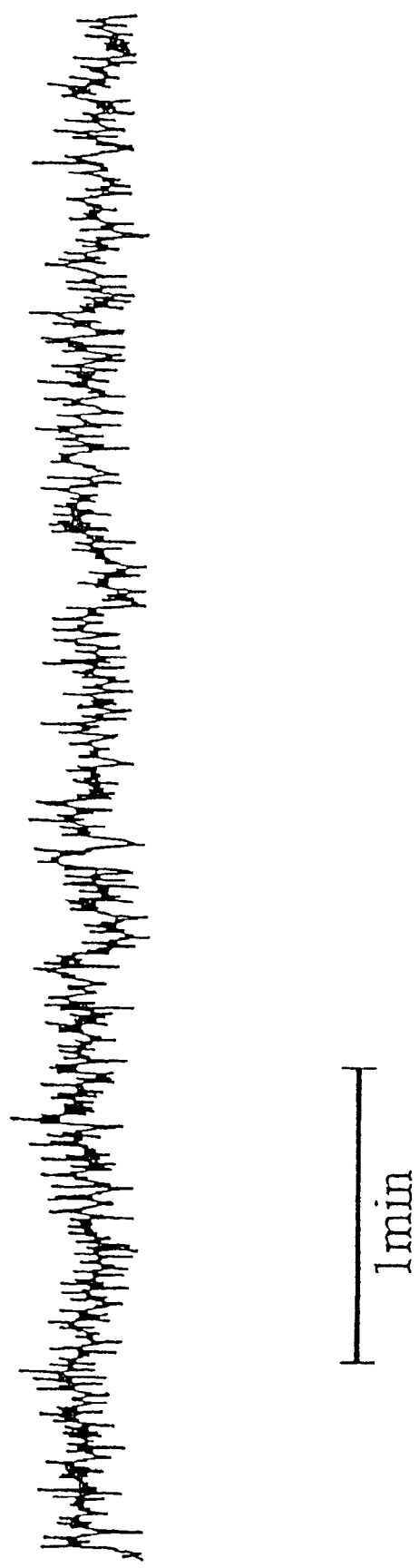
FIG. 1 shows the time-series change of $Ca^{2+}$ concentration in neurons without any additive.

Theanine in this invention is L-glutamic-γ-ethylamide or a mixture comprising L-glutamic-γ-ethylamide and its derivative.

L-glutamic-γ-ethylamide derivatives are, for example,

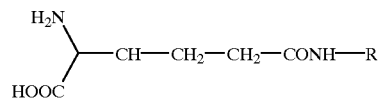

[R:CH₃, C₂H₅, CH₂(CH₂)ₙCH₃ (n = 1~8)]

-continued
[R:CH₃, C₂H₅, CH₂(CH₂)ₙCH₃ (n = 1~8)]

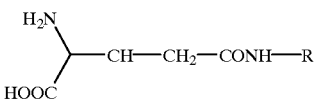

[R:CH₃, C₂H₅, CH₂(CH₂)ₙCH₃ (n = 1~8)]

Theanine has now been approved as a food additive and is being consumed daily. Therefore, there is not a fear for adverse reactions and its safety is obvious.

It is also known that theanine passes through the blood-brain barrier relatively easily compared to many amino acids contained in food and its intestinal absorption is high. This is probably attributable to the ethyl radical in the theanine structure making the substance oil-soluble.

Theanine is available by various publicly known methods. In other words, it is biosynthesized in plant or microorganism culture, extracted from tea leaves or synthesized chemically. For example, it is industrially available by heating L-glutamic acid to L-pyrrolidone carboxylic acid, which is then made into copper L-pyrrolidone carboxylate and allowed to react with anhydrous ethylamine. Copper is removed finally.

Theanine may reach reurons in the brain through the blood-brain barrier by any of the oral, intravascular or direct administration. Since theanine passes through the blood-brain barrier relatively easily and, moreover, its absorption in the intestine is high as mentioned above, it can act on neurons effectively even being administered orally. Its effects become higher if it is intravascularly or directly administered.

In case of oral administration, while theanine may be given by dissolving in purified water or a physiological salt solution as it is, it is also possible to administer the substance by a known method in forms of tablet, capsule, granule, powder, syrup or drink by adding a vehicle, binder, disintegrator, lubricant, stabilizer or corrigent. The above mentioned theanine may be offered as brain function improving food or drink by adding various additives to the substance, which is then sterilized by the method such as autoclaving regulated by the food sanitation law and to freeze-drying.

In case of intravascular administration, theanine may be dissolved in a physiological salt solution or glucose solution for injection.

The minimum effective dose of theanine affecting cerebral neurons through the blood-brain barrier is considered to be 0.17 mg/kg body weight by intravascular administration. This is based on the result of the reference experiment to be mentioned later confirming that an intravenous injection of 1 μmol (0.17 mg) of theanine per kg body weight was absorbed in the brain to show effects. This result suggests that theanine is absorbed into the brain and shows anti-glutamic effect and glutamin receptor blocking effect when it is administered at the minimum of 0.17 mg/kg body weight.

In case of oral administration, the minimum effective dose is calculated as about 0.20 mg/kg body weight (0.17/0.83) considering the result of the reference experiment given later and the intestinal absorption rate of 30–83% (Dietetics Handbook; Gihodo Shuppan, 1985) for an amino acid mixture with similar characteristics to theanine. However, it is quite possible that the minimum effective dose is lower than this value as the intestinal absorption of theanine is higher than that of other amino acids.

According to this invention, theanine arriving at the neurons through the blood-brain barrier binds to NMDA receptors closely associated with the brain function such as memory and learning, increases intracellular $Ca^{2+}$ concentration as well as synaptic plasticity including long-term potentiation of the neurons leading to plastic change of the neurons or neural circuit as demonstrated by the experimental result. Thus, theanine when allowed to act on the cerebral neurons by oral, intravascular or direct administration, or by some other means, is effective for treatment, improvement and prevention of brain dysfunction, symptoms such as Alzheimer's disease, Parkinson's disease and senile dementia pathophysiologically associated with dysfunction as well as traumatic nervous disorders.

There are active and inactive neurons in voluntary firing and the brain function improving effect of theanine is considered such that it stimulates inactive neurons and induces their synchronous firing with active neurons.

Moreover, theanine arriving at the cerebral neurons through the blood-brain barrier inhibits glutamate excitotoxicity. Therefore, if theanine is allowed to affect the cerebral neurons by oral, intravascular or direct administration or by some other means when intracerebral glutamic acid has increased markedly due to brain ischemia, etc., it can inhibit glutamate excitotoxicity as well as delay neuronal death due to glutamic acid leakage from the dead cells preventing expansion of neuronal death. It is thus effective for treating glutamic acid-induced brain disorders such as brain apoplexy including infarct and hemorrhage as well as brain ischemia accompanying brain surgery and wound.

Furthermore, as mentioned above, theanine can block NMDA receptors, which are glutamic acid receptors, by binding with them. In other words, theanine inhibits transmission of excessive excitation by glutamic acid to neurons and, thus, administration of theanine to brain neurons in advance is effective for prevention of glutamic acid-induced brain disorders such as brain apoplexy including infarct and hemorrhage as well as brain ischemia accompanying brain surgery and wound.

It is considered that the inhibitory effect (antagonistic effect) of theanine on glutamate excitotoxicity such as this derives from competitive action of theanine; theanine acts agonistically to NMDA glutamic acid receptors similarly to glutamic acid but the action of the former is much weaker than that of the latter and hence theanine acts competitively to NMDA glutamic acid receptors when theanine and glutamic acid are coexisting. Preventive effect of theanine on neurons and glia cells is also attributable to the above mechanism.

DESCRIPTION OF PREFERRED EMBODIMENTS

EXAMPLE 1

In this example, theanine was given by a single administration to the primary cultured rat cerebral cortical neurons and its effect on glutamic acid receptors, NMDA receptors in particular, in the neurons was examined by measuring the time-series change in $Ca^{2+}$ concentration in the cells using fluorescent $Ca^{2+}$ sensitive dye, fura-2.

[Culture of rat cerebral cortical cells]

The cerebral cortex was excised from the rat fetal brain obtained from the rat in 18-day pregnancy and the hippocampus and the mid-brain were removed from the block.

The obtained block was minced by a knife and transferred into a centrifugation tube followed by addition of 5 ml DMEM culture medium (1.34% DMEM: Dulbecco's Modified Eagle Medium, 0.12% $NaHCO_3$, 5000 U/l penicillin, 0.001% streptomycin, 0.01% pyruvate, and 5% new born calf serum, and 5% inactivated horse serum added at the time of use). The mixture was allowed to stand for 1–2 minutes and, after eliminating the supernatant, 5 ml of papain digestion anescedia were added and incubated at 37° C. for 15 minutes while shaking at 5-minute intervals. The procedure was repeated twice and the supernatant was discarded. 5 ml of DMEM culture medium containing the sera were added and pipetted to disperse the cells. Then, the cells were transferred to another centrifuge tube through a sterilized lenz paper filter and centrifuged at 1000 rpm for 5 minutes. The supernatant was discarded and 5 ml of DMEM culture medium containing the sera were added again.

Then, the cells were stained by 0.5% tripan blue and counted on a blood cell counting chamber. Also, a plate was prepared by adhering a cover glass to the bottom of 8-well silicon frame where the wells (8×11 mm inner diameters) were coated by polyethylene imine and the above isolated cells were seeded at a fixed concentration and cultured by exchanging the culture solution every few days.

[Theanine administration]

After changing the cell culture medium to a buffer containing 0.8 mM $Mg^{2+}$ on the 15th day, the culture medium was changed to BSS solution (130 mM NaCl, 5.4 mM KCl, 1.8 mM $CaCl_2$, 5.5 mM glucose and 20 mM HEPES adjusted to pH 7.4 by NaOH) containing 0.8 mM $Mg^{2+}$. Fura-2 was taken up by the cells and the time-series change in the intracellular $Ca^{2+}$ concentration was measured using a multi-point simultaneous observation device for intracellular $Ca^{2+}$ concentration developed by Kudo, et. al. in 1986. Then, 800 μM theanine (commercial product; 99% purity) were added to the culture cells with fura-2 and the change in $Ca^{2+}$ concentration in the neurons was measured. Meanwhile, 50 μM D-APV known as a specific inhibitor for NMDA receptors were added to the culture cells with fura-2 to block the receptors by prior binding followed by addition of 800 μM theanine to measure the time-series change in $Ca^{2+}$ concentration in the neurons. Furthermore, the added D-APV and theanine were once removed from the neurons and 800 μM theanine were added again to examine the change in $Ca^{2+}$ concentration in the neurons.

Figure 2:
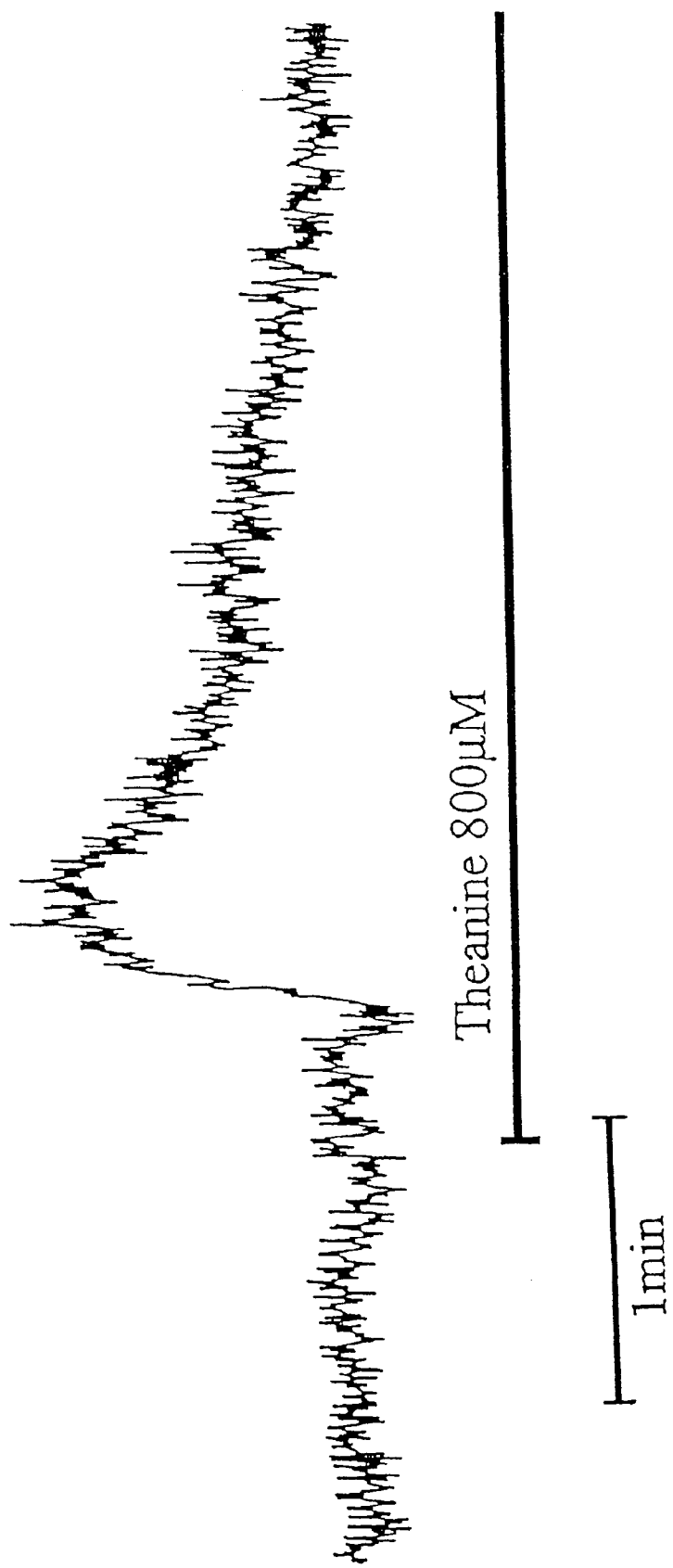
FIG. 2 shows the time-series change of $Ca^{2+}$ concentration in neurons with addition of 800 $\mu$M theanine.

FIGS. 1 and 2 show the measurement results.

[Result]

First of all, intracellular $Ca^{2+}$ concentration did not show any change when the cells were cultured in a medium without any additive (FIG. 1). When 800 μM theanine were added, a big increase in intracellular $Ca^{2+}$ concentration was observed temporarily (FIG. 2). However, addition of D-APV to block NMDA receptors in prior to theanine addition did not show any increase in intracellular $Ca^{2+}$ concentration similarly to the result in FIG. 1. Then, addition of theanine after elimination of D-APV and theanine from the neurons gave a similar result as in FIG. 2 indicating an increase in intracellular $Ca^{2+}$ concentration.

These results demonstrated that theanine bound to glutamic acid receptors, NMDA receptors in particular, in the neurons reversibly inducing an increase in intracellular $Ca^{2+}$ concentration as well as plastic change in synapses acting effectively on memory and learning.

EXAMPLE 2

In this example, theanine was administered to the primary cultured rat cerebral cortical neurons continuously at a dose lower than that in the above example 1 and the time-series change of $Ca^{2+}$ in the cells was measured to examine effective concentration of the substance to act as a brain function improving agent.

[Culture of rat cerebral cortical neurons]

The same procedure as in the example 1 was carried out.

[Administration of theanine]

After exchanging the above culture medium by a buffer containing 0.8 mM $Mg^{2+}$, fura-2 was consumed by the cells. Theanine (commercial product; 99% purity) was added to the culture cells continuously by perfusion to make its concentration 50 μM initially and then 200 μM in the same cells. The added theanine was washed out each time after a fixed period of time and $Ca^{2+}$ concentration in the neurons was measured.

Figure 3:
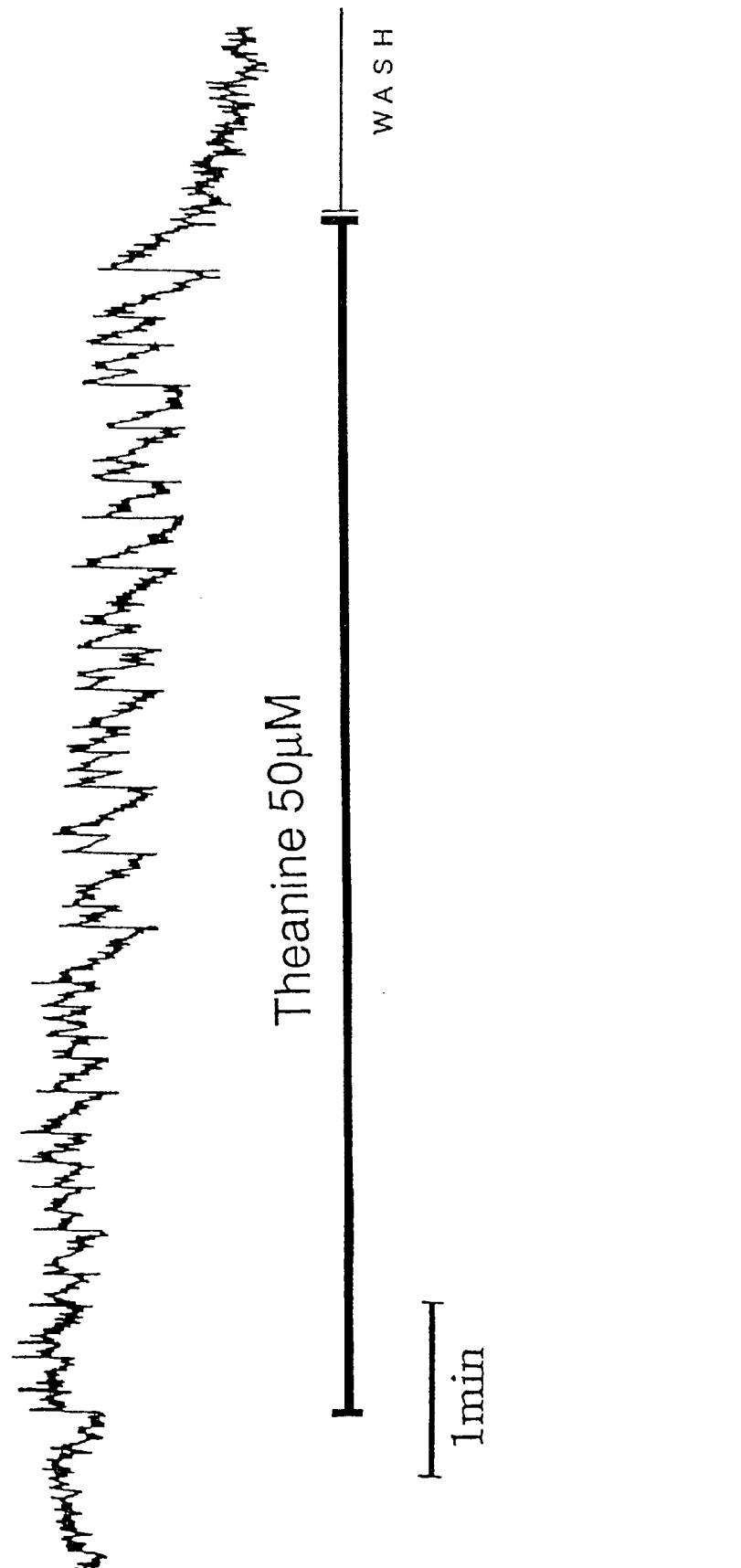
FIG. 3 shows the time-series change of $Ca^{2+}$ concentration in neurons with continuous addition of theanine to make 50 $\mu$M concentration.
Figure 4:
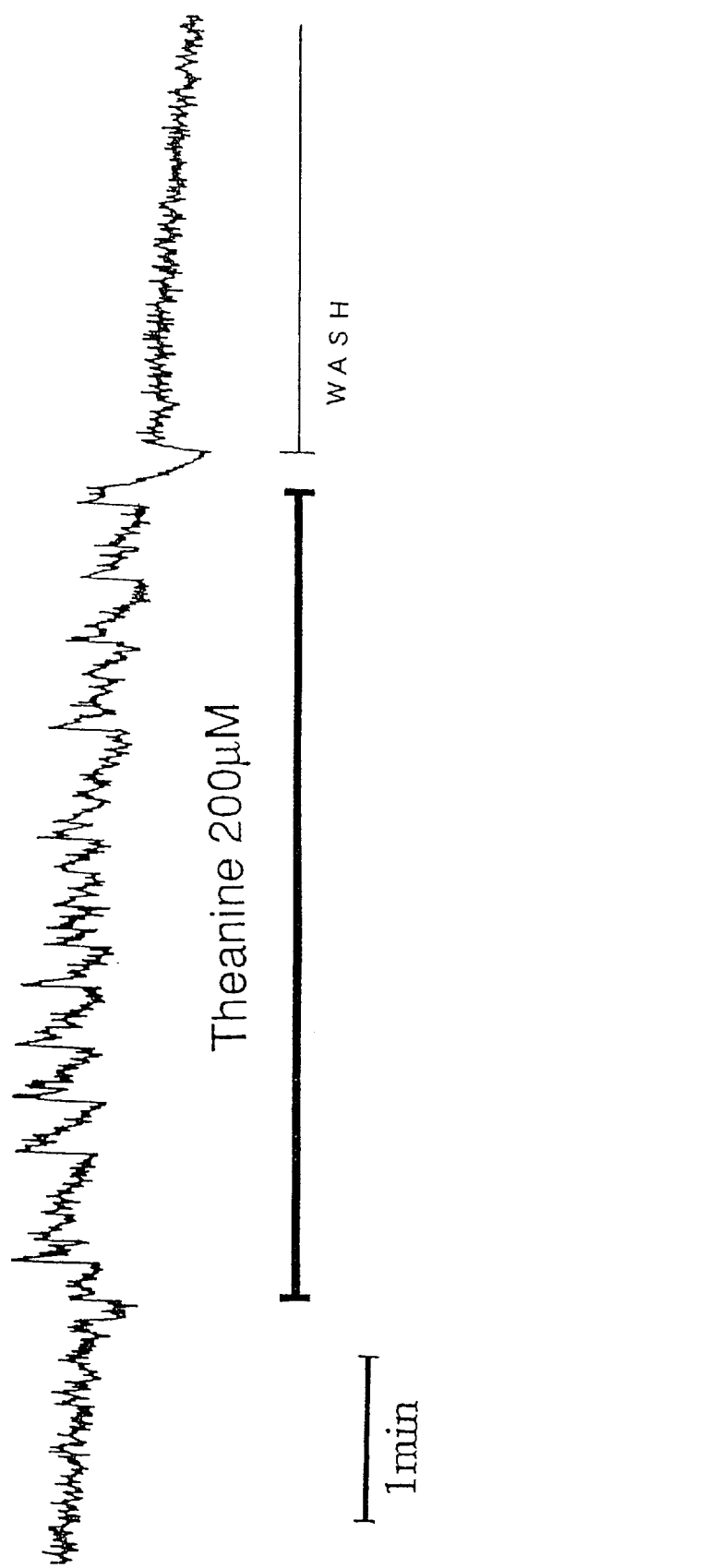
FIG. 4 shows the time-series change of $Ca^{2+}$ concentration in the same neurons as in FIG. 3 with continuous addition of theanine to make 200 $\mu$M concentration.
Figure 5A:
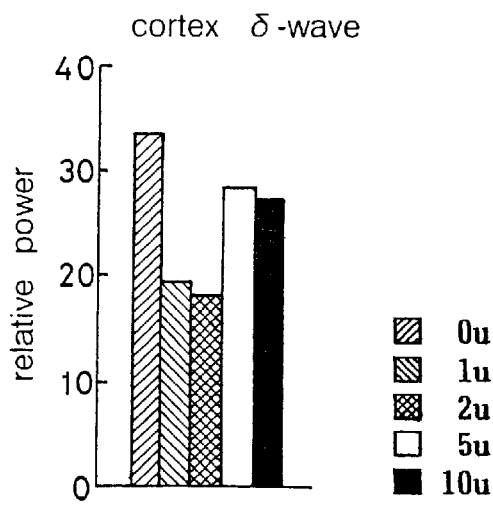
FIGS. 5–23 below show the results of the reference experiments.
Figure 5B:
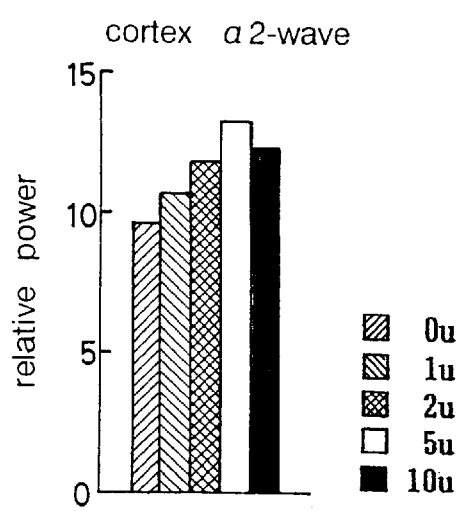
Figure 5C:
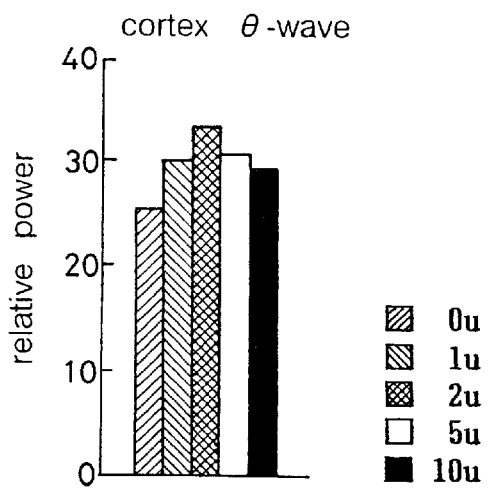
Figure 5D:
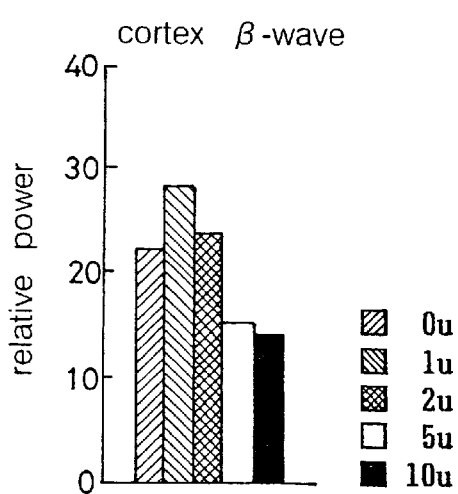
Figure 5E:
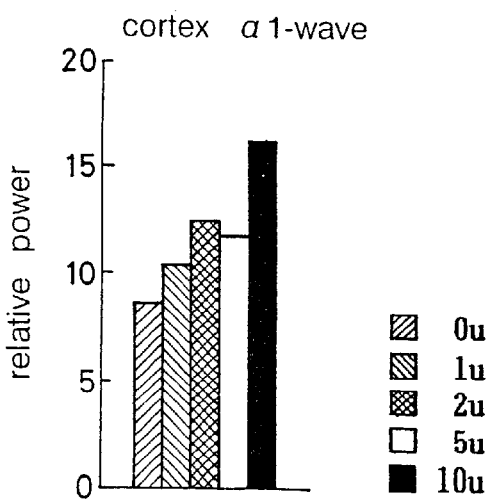
Figure 6A:
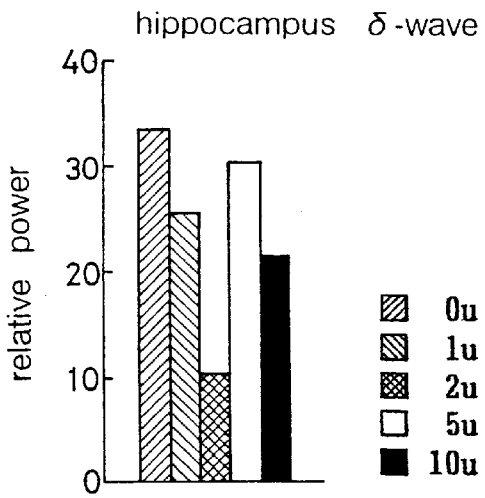
Figure 6B:
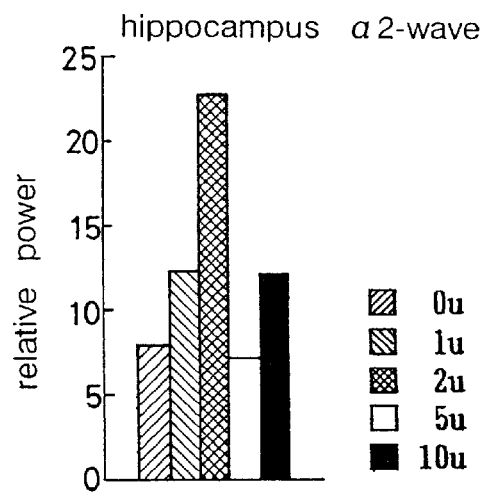
Figure 6C:
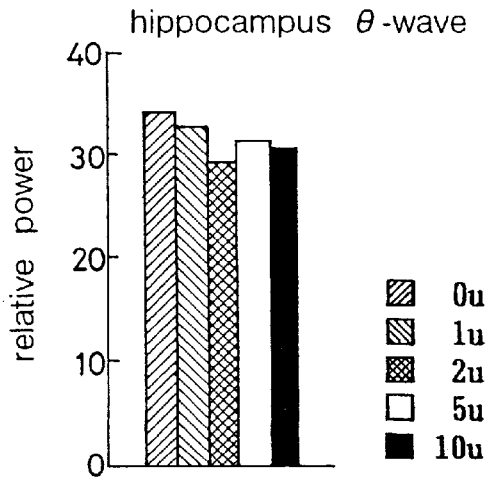
Figure 6D:
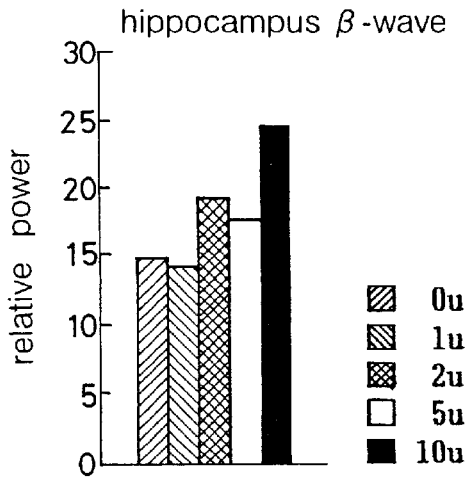
Figure 6E:
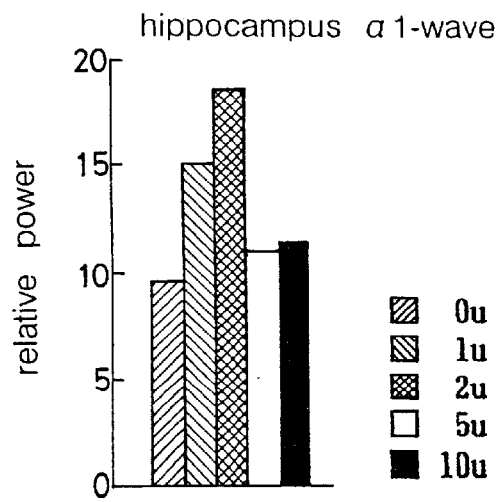
Figure 7A:
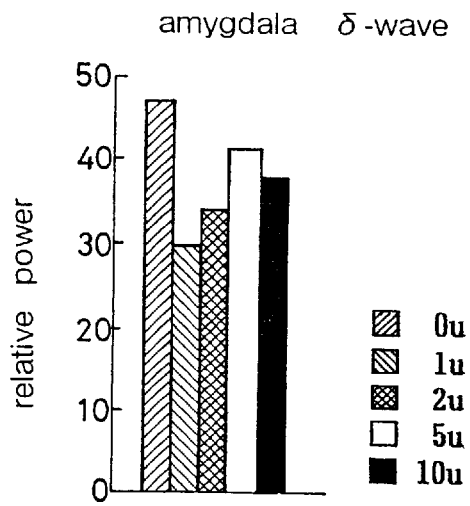
Figure 7B:
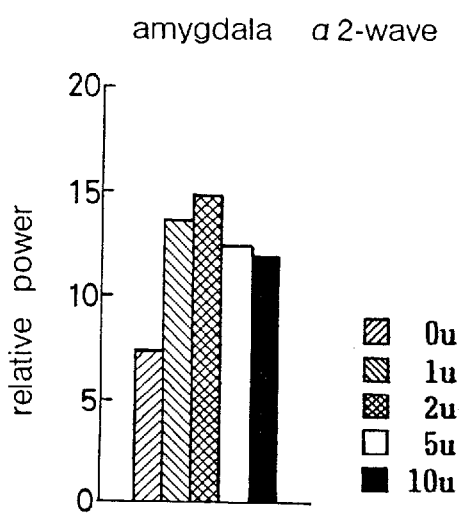
Figure 7C:
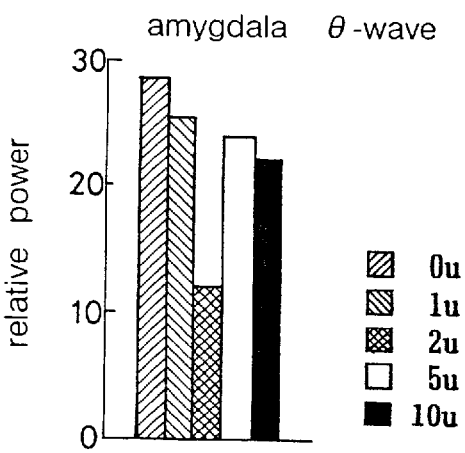
Figure 7D:
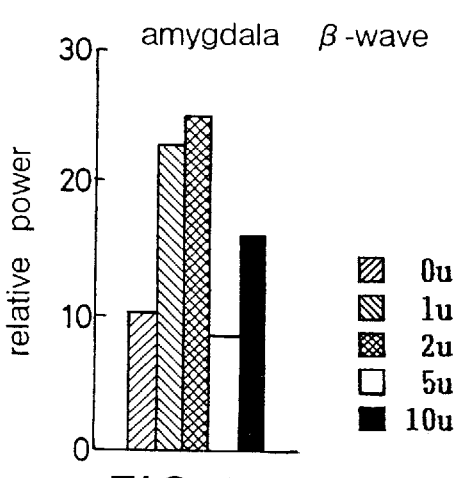
Figure 7E:
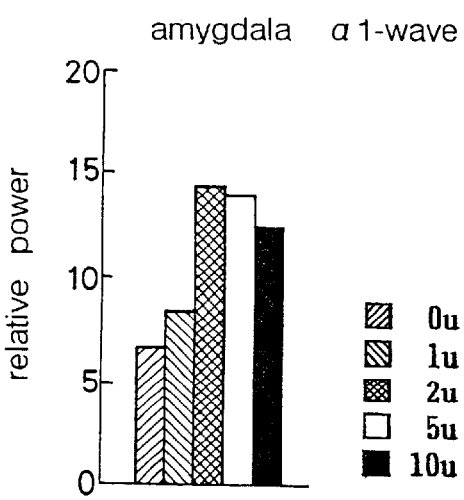
Figure 8A:
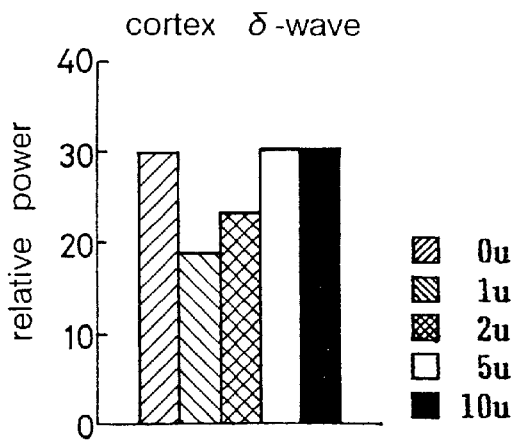
Figure 8B:
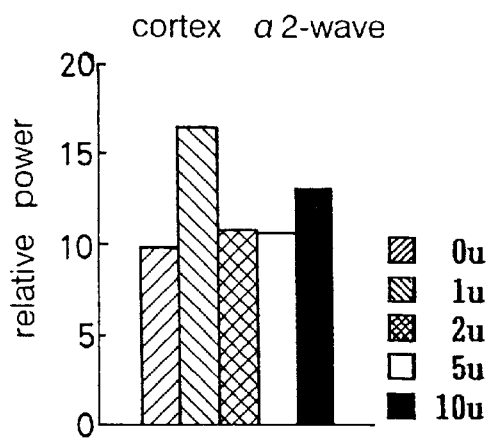
Figure 8C:
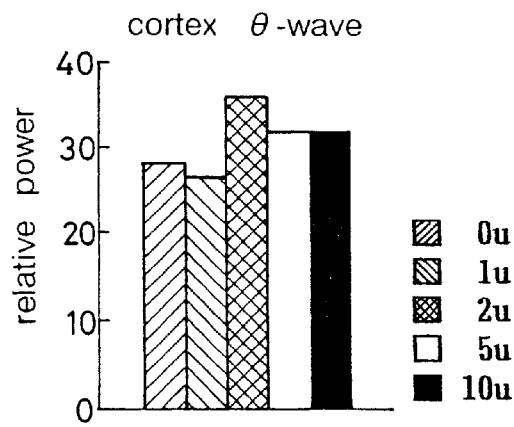
Figure 8D:
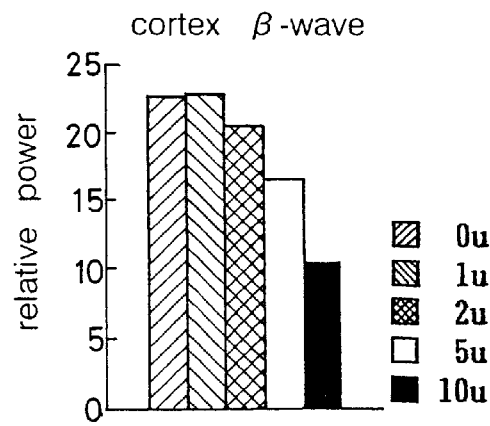
Figure 8E:
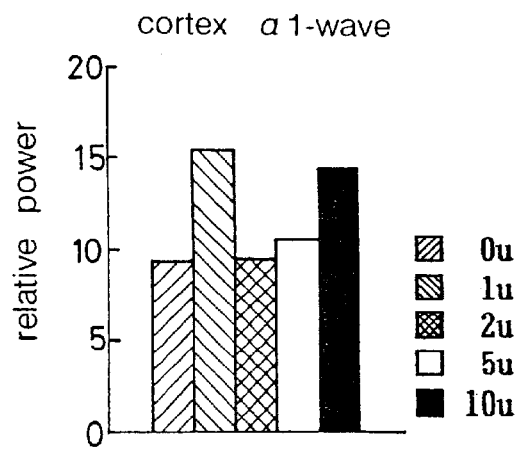
Figure 9A:
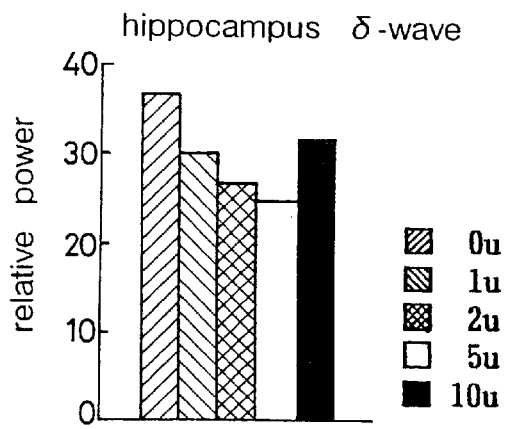
Figure 9B:
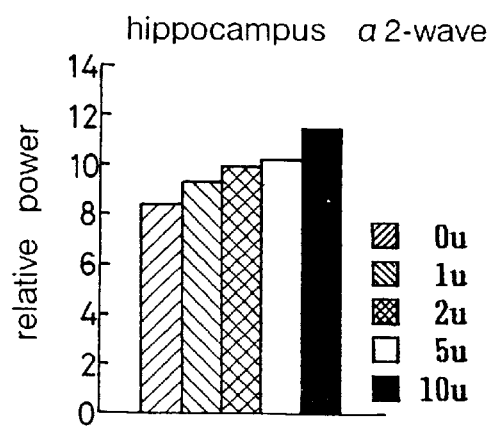
Figure 9C:
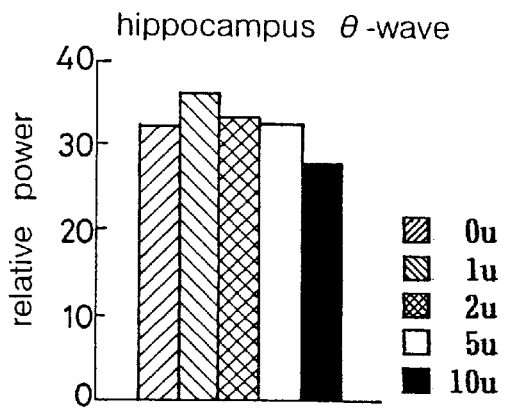
Figure 9D:
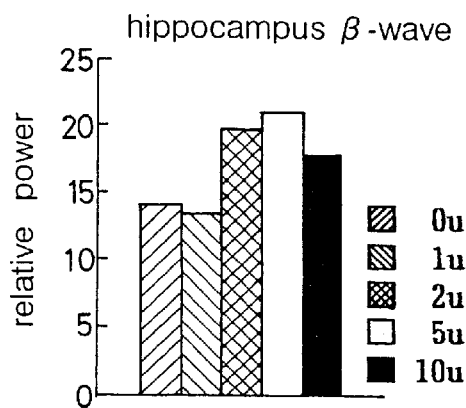
Figure 9E:
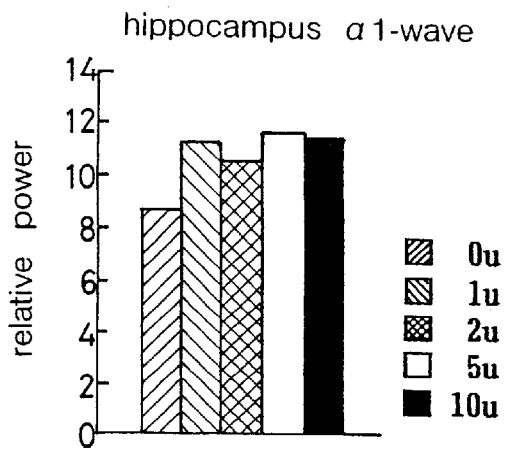
Figure 10A:
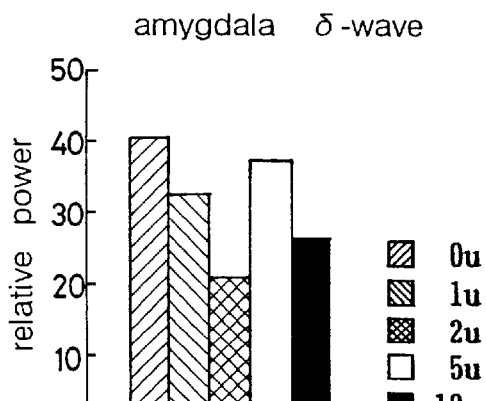
Figure 10B:
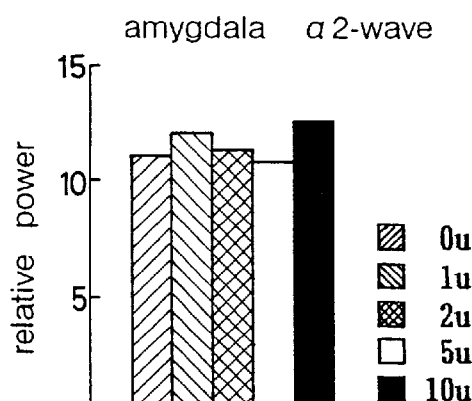
Figure 10C:
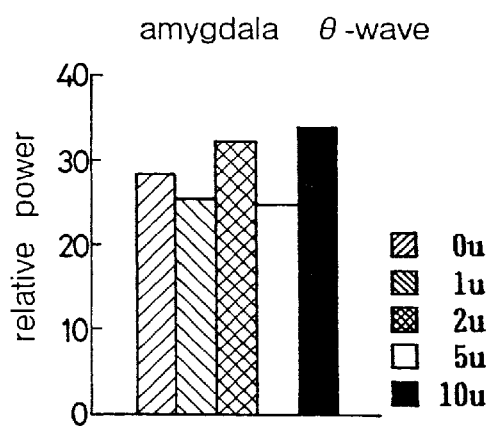
Figure 10D:
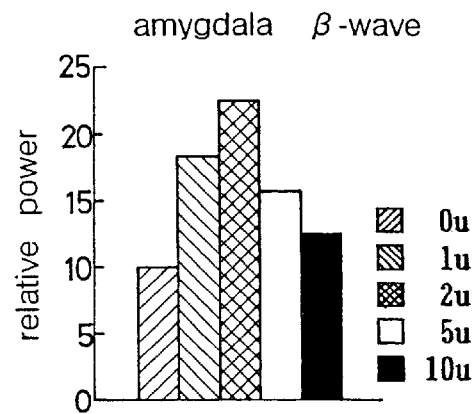
Figure 10E:
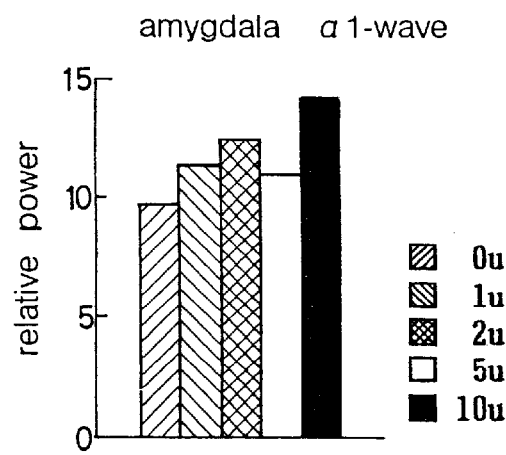
Figure 11A:
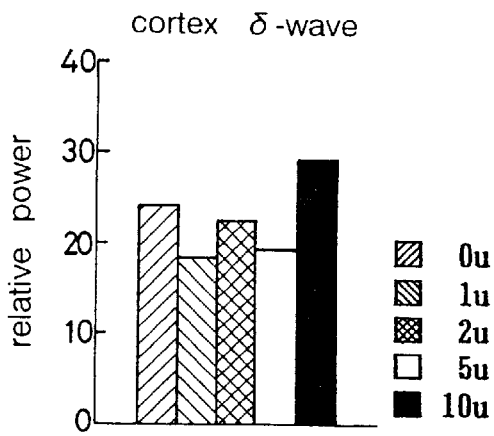
Figure 11B:
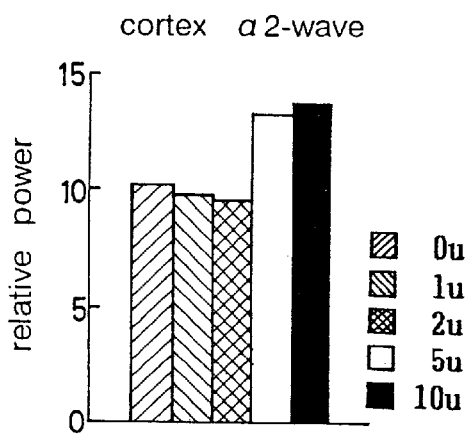
Figure 11C:
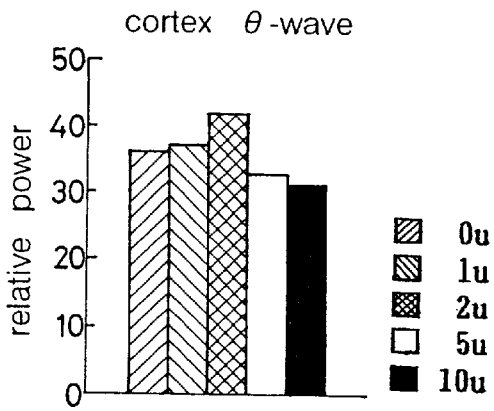
Figure 11D:
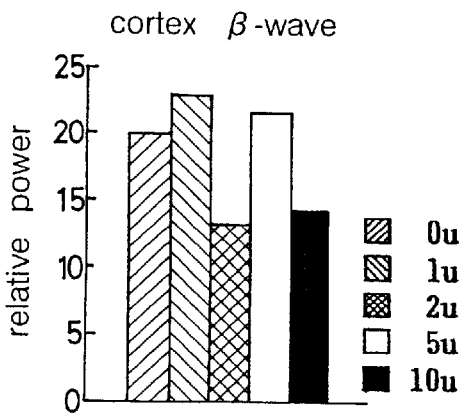
Figure 11E:
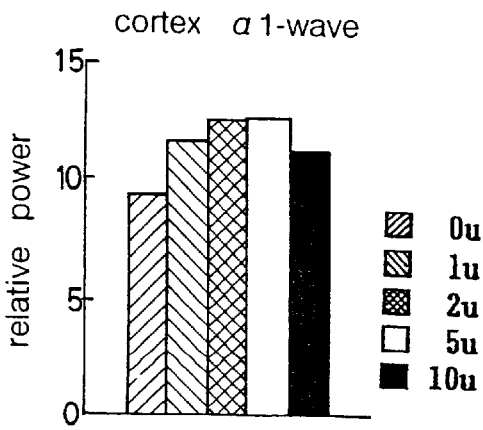
Figure 12A:
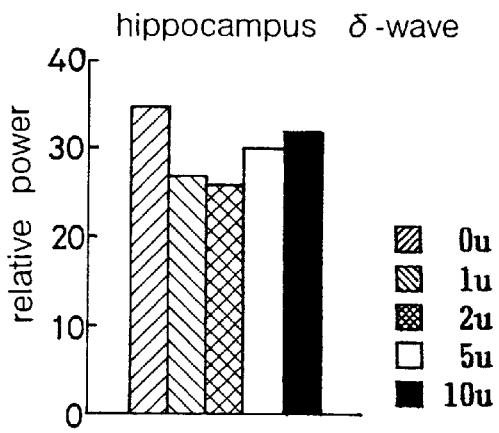
Figure 12B:
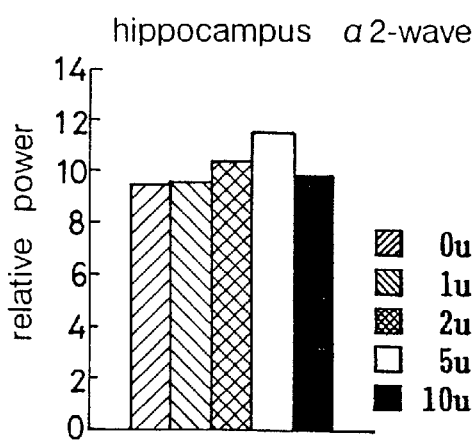
Figure 12C:
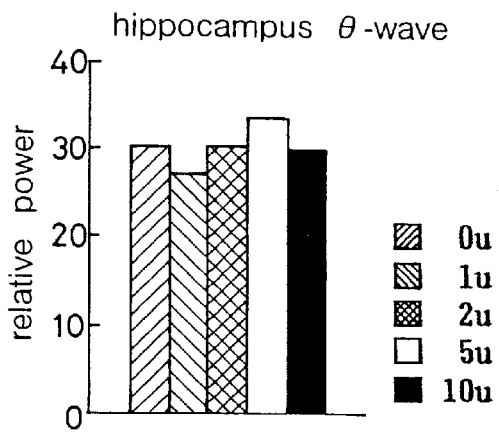
Figure 12D:
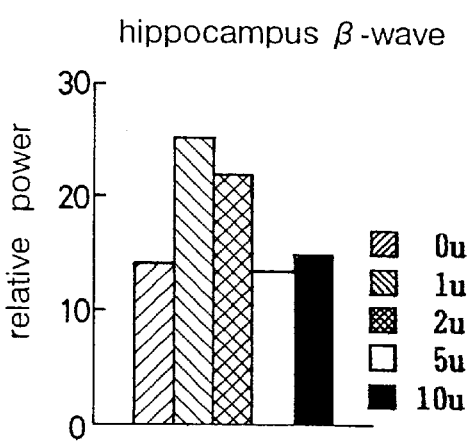
Figure 12E:
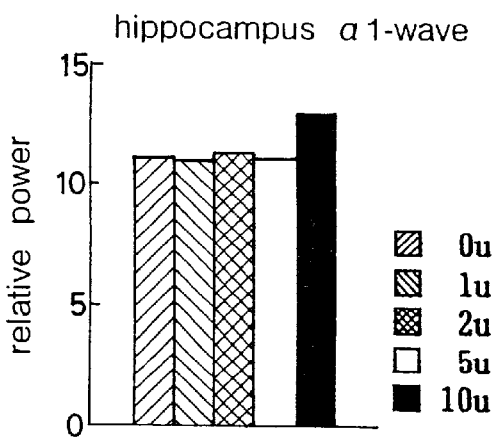
Figure 13A:
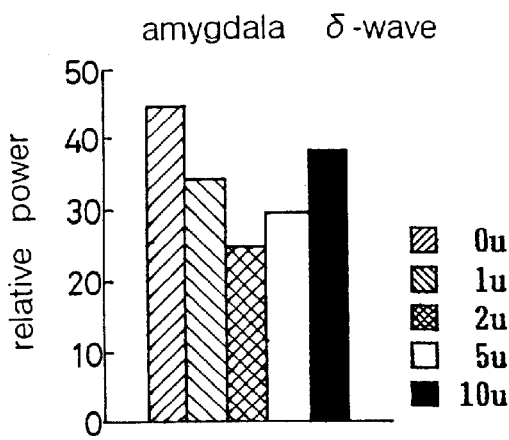
Figure 13B:
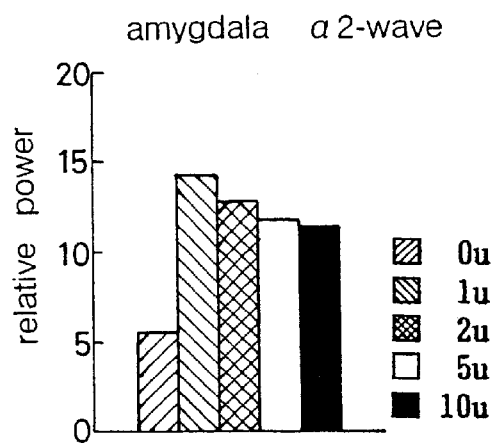
Figure 13C:
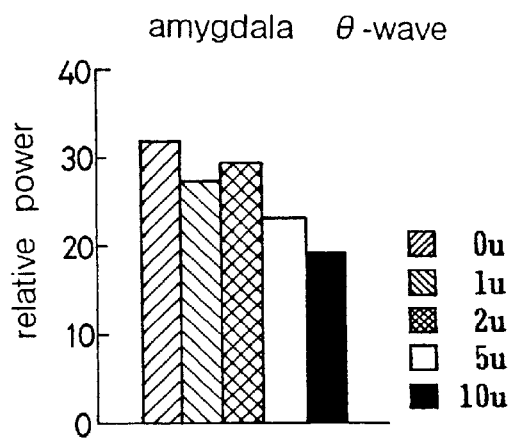
Figure 13D:
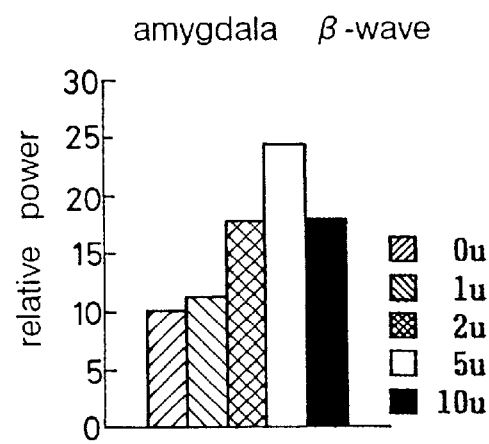
Figure 13E:
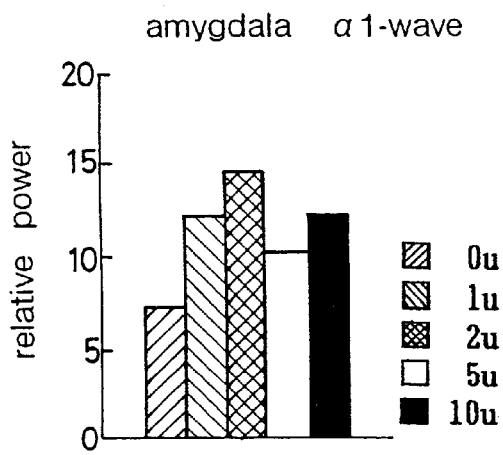
Figure 14A:
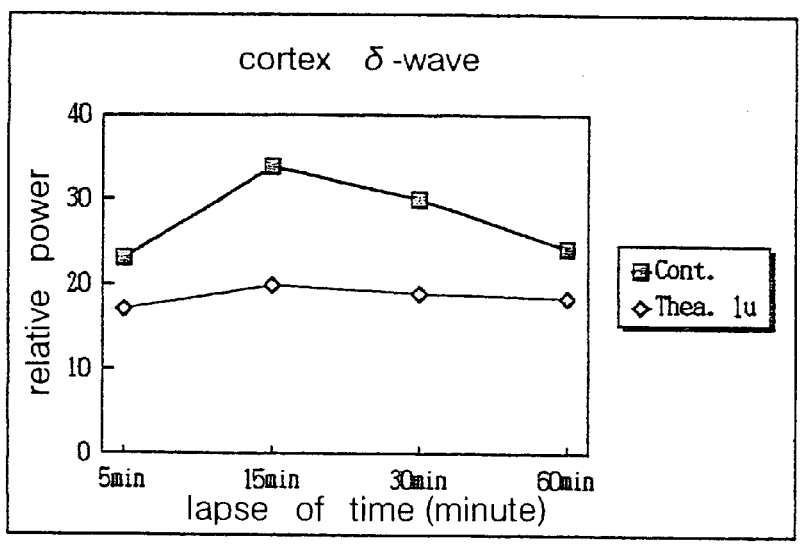
Figure 14B:
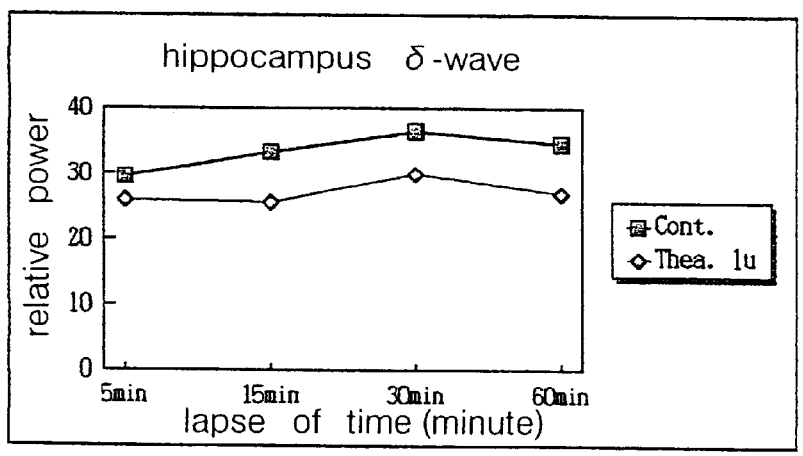
Figure 14C:
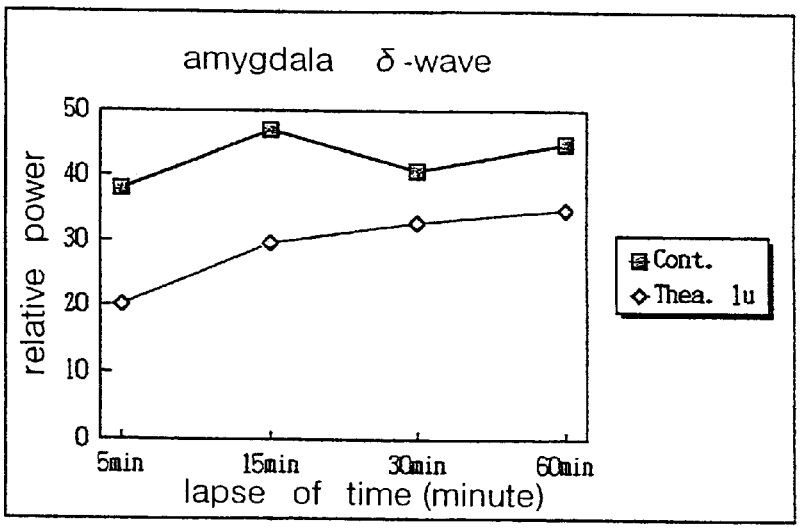
Figure 15A:
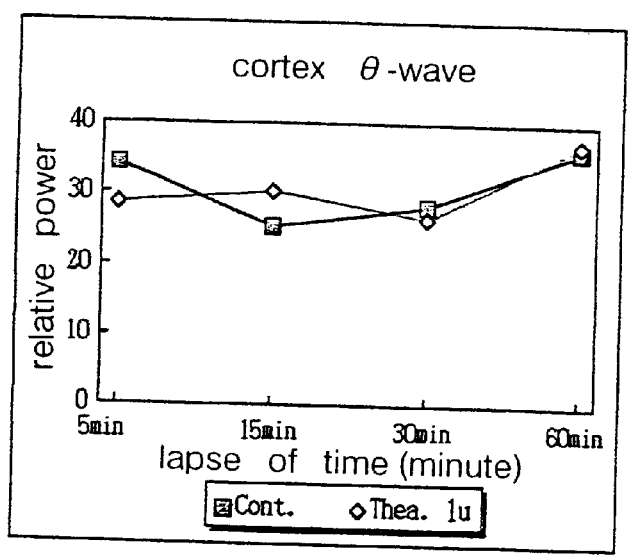
Figure 15B:
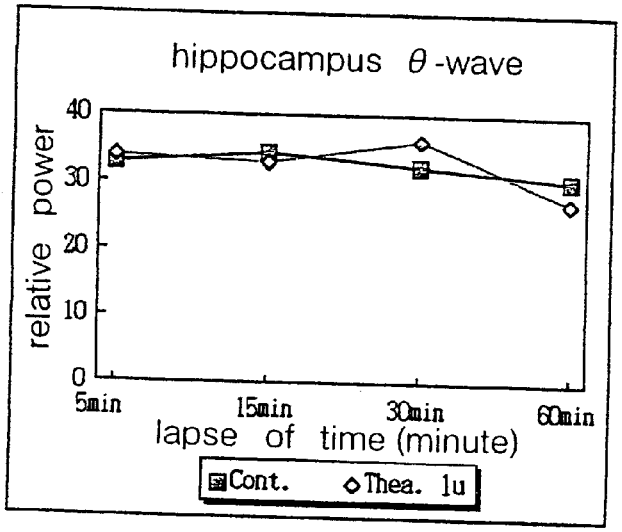
Figure 15C:
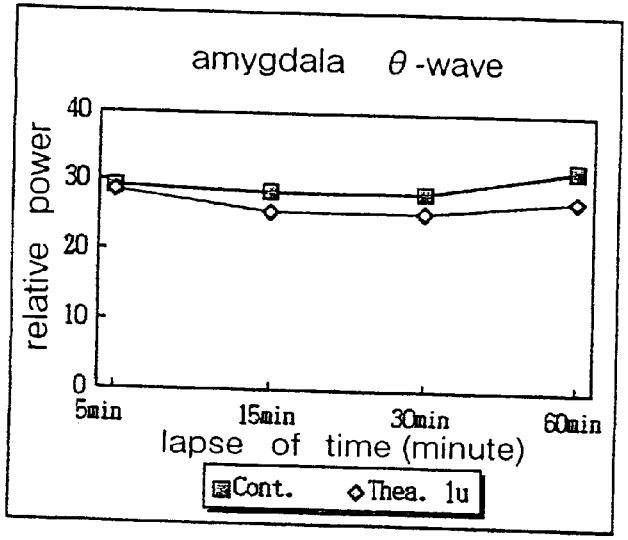
Figure 16A:
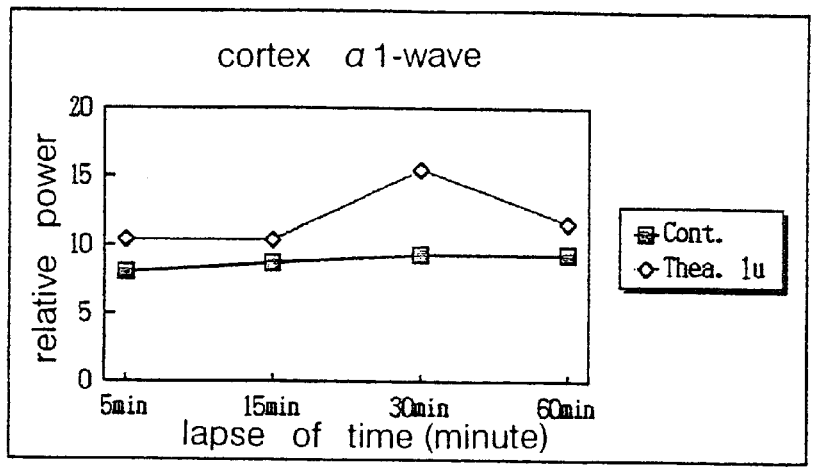
Figure 16B:
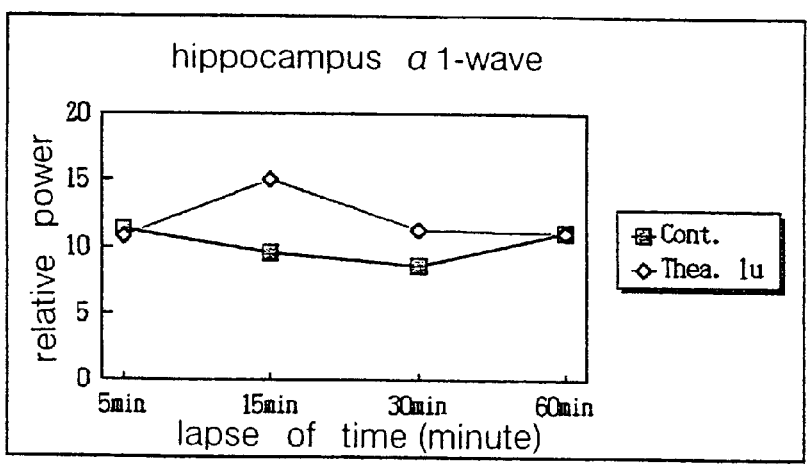
Figure 16C:
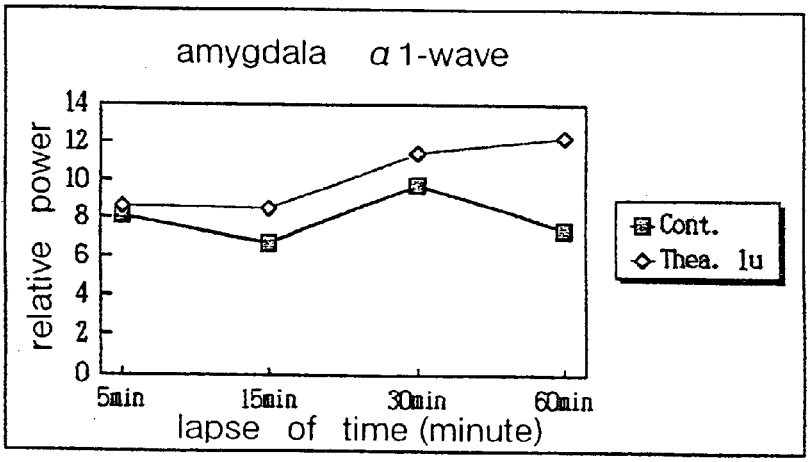
Figure 17A:
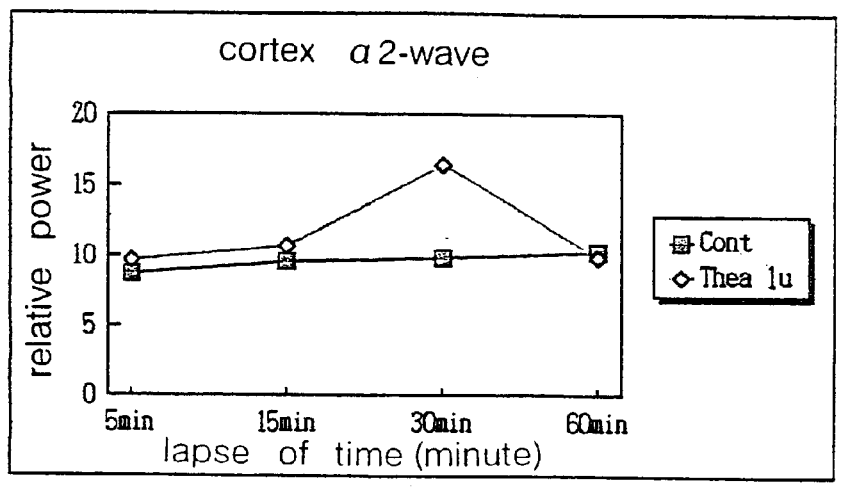
Figure 17B:
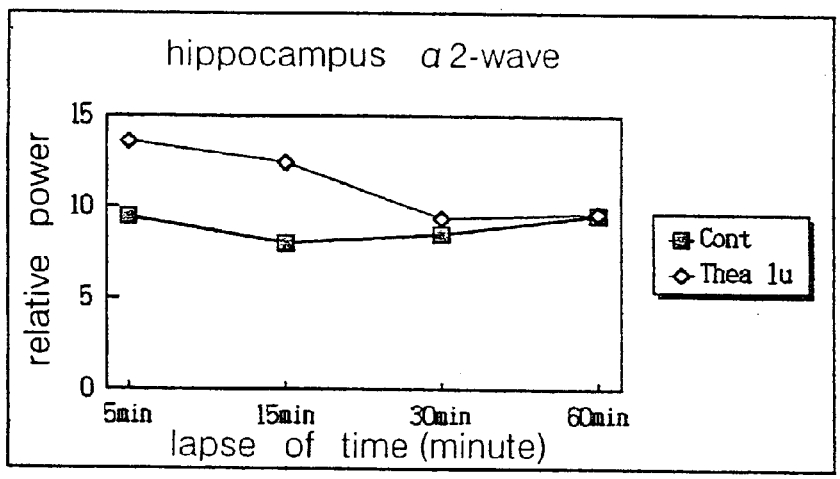
Figure 17C:
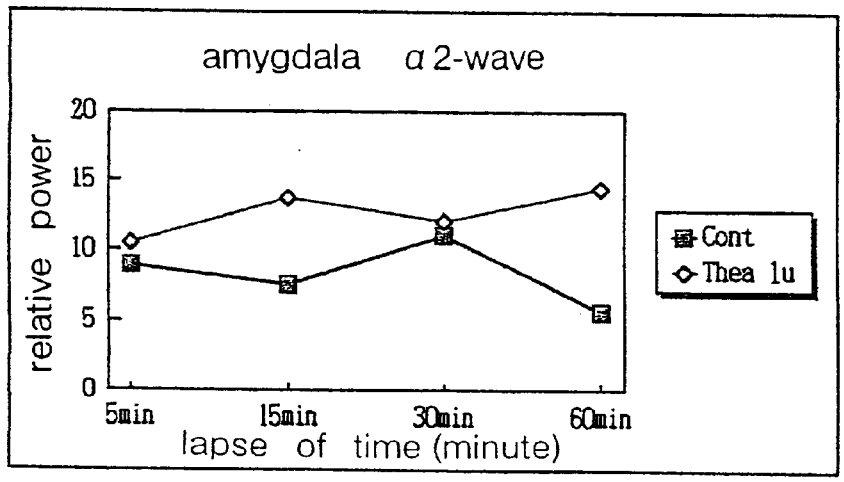
Figure 18A:
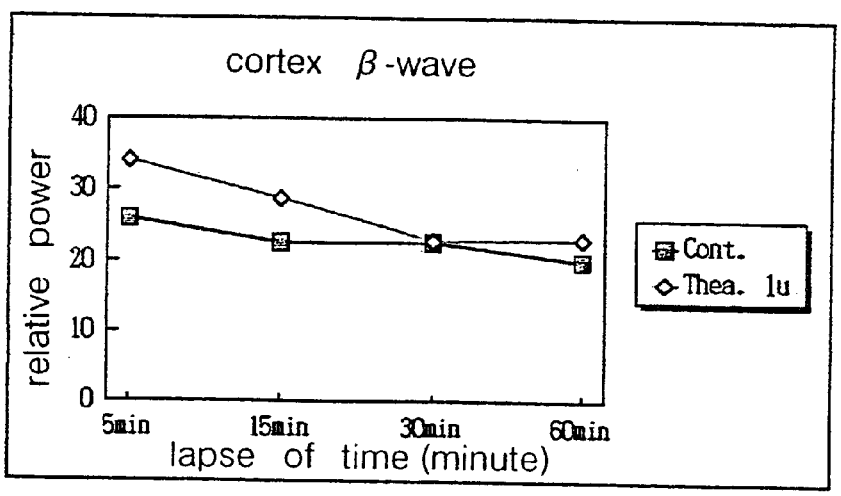
Figure 18B:
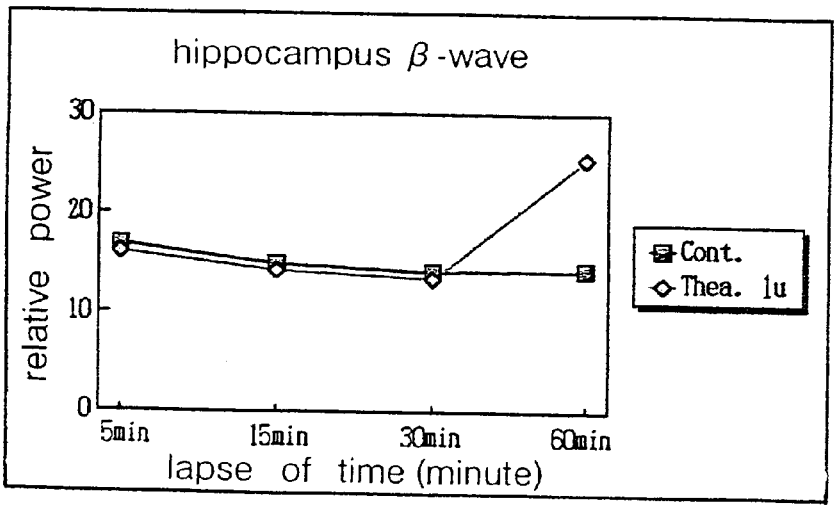
Figure 18C:
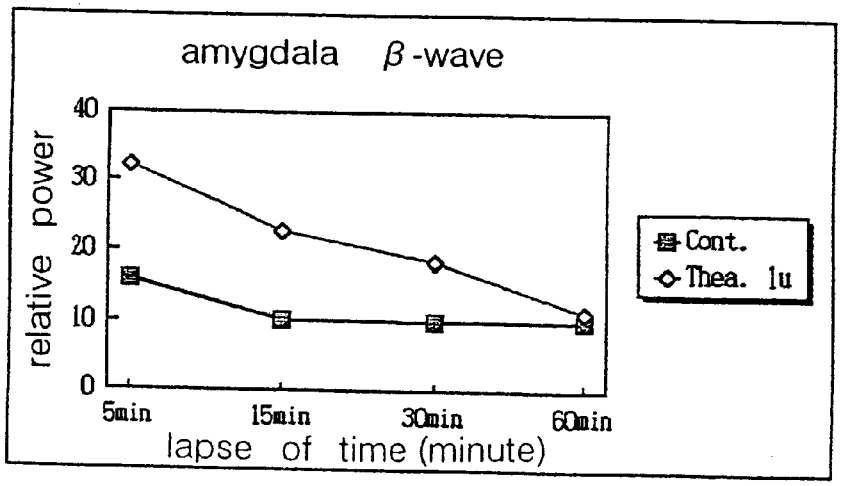
Figure 19A:
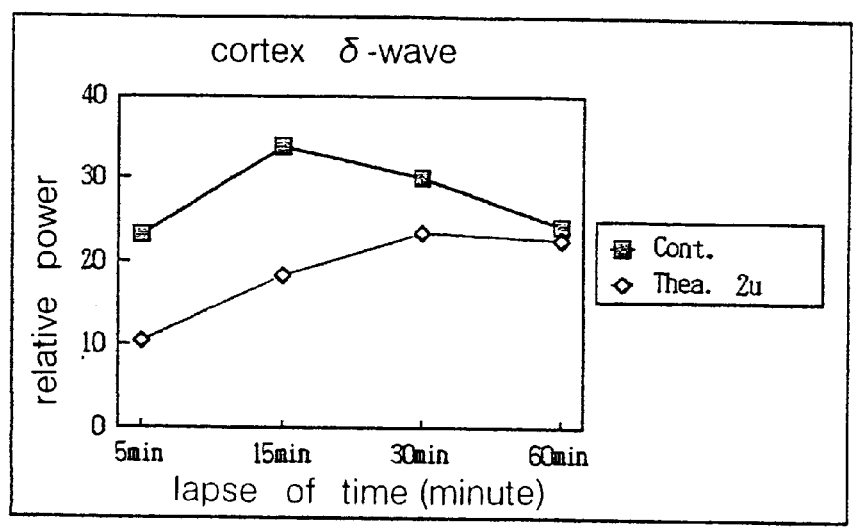
Figure 19B:
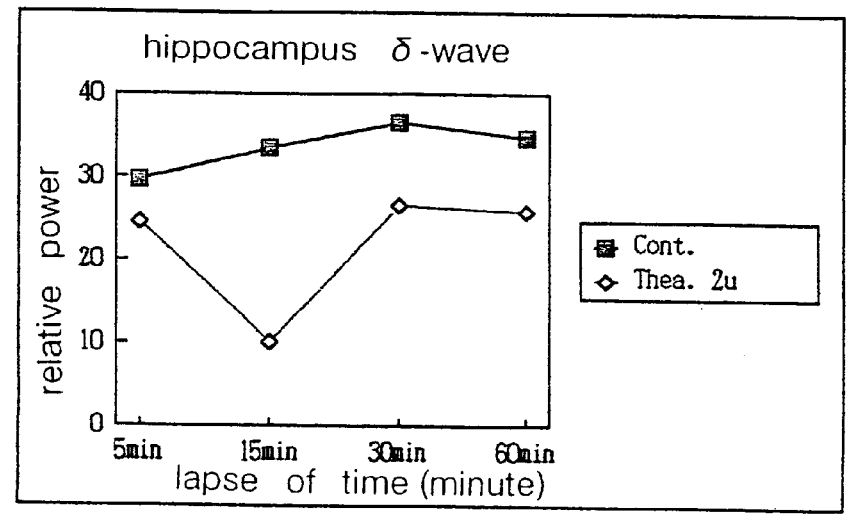
Figure 19C:
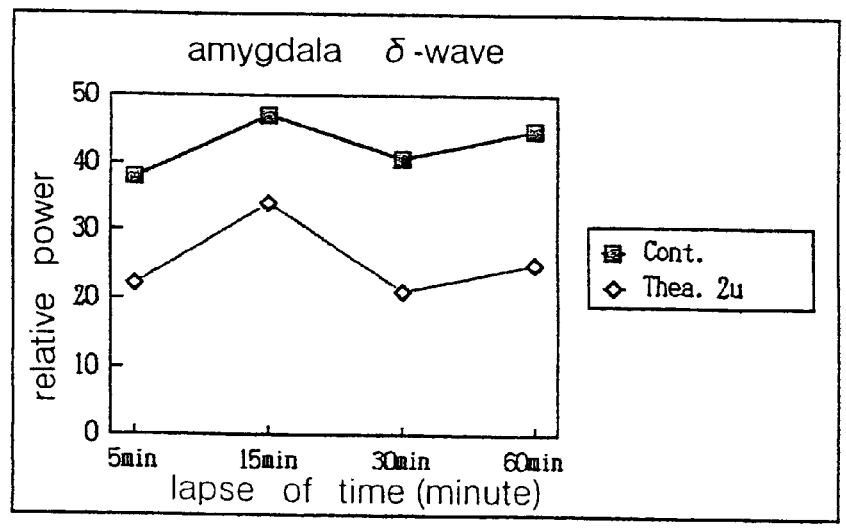
Figure 20A:
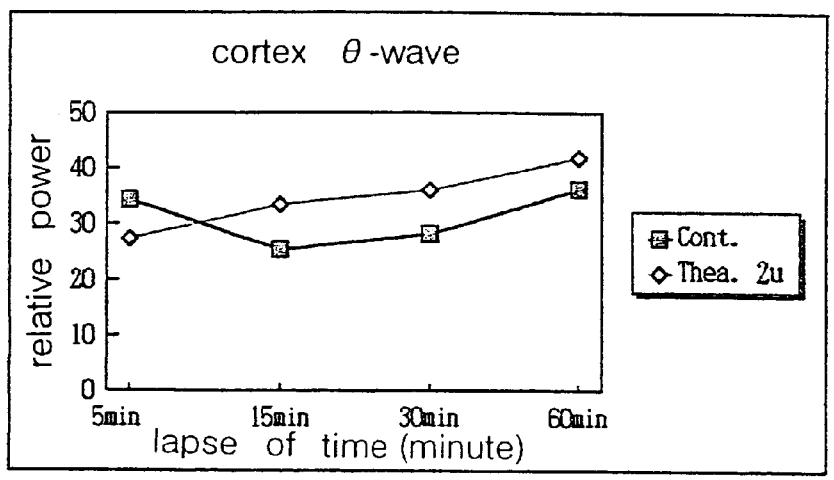
Figure 20B:
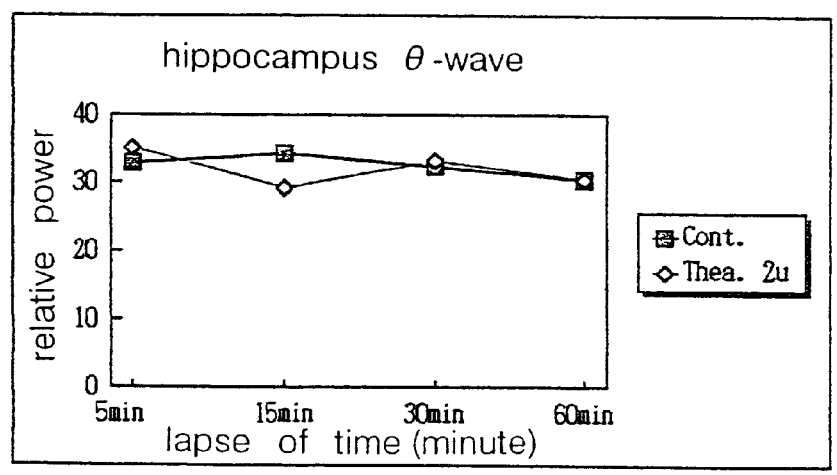
Figure 20C:
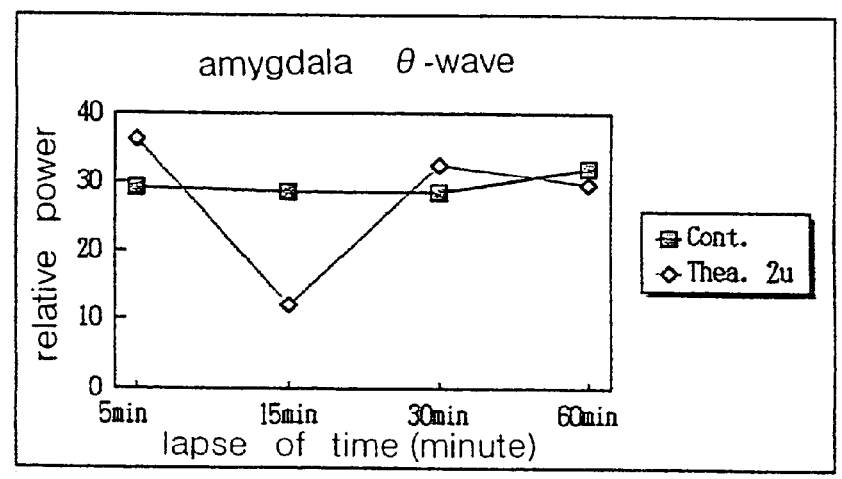
Figure 21A:
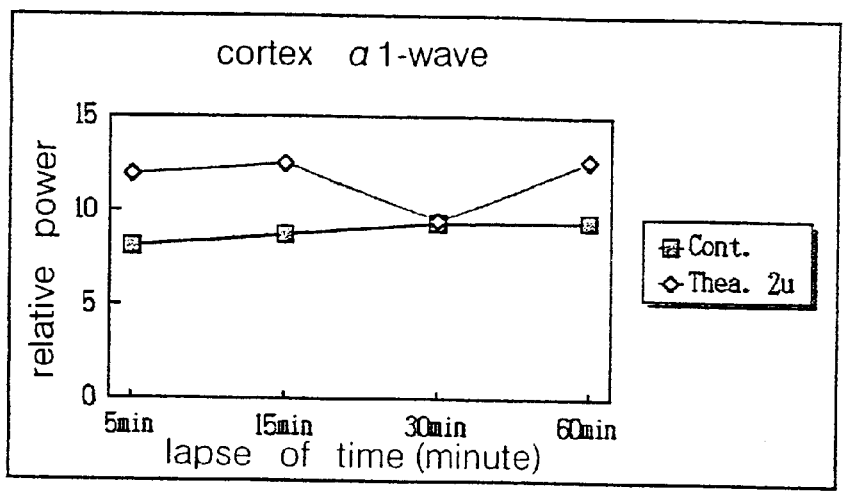
Figure 21B:
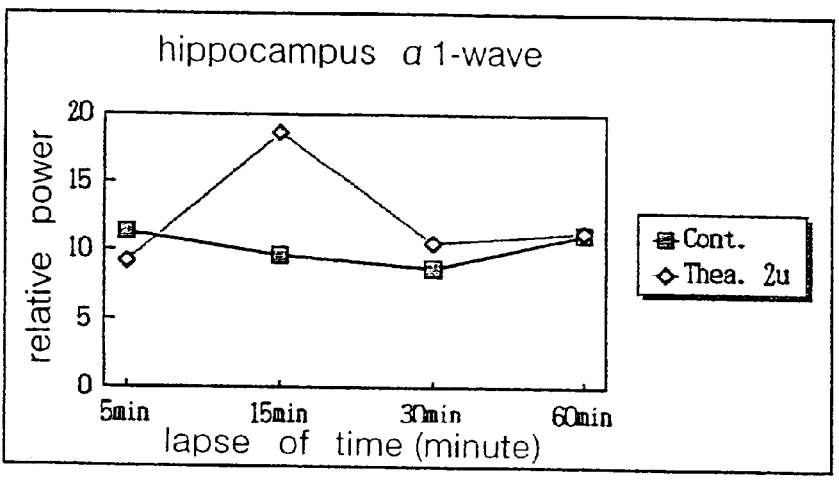
Figure 21C:
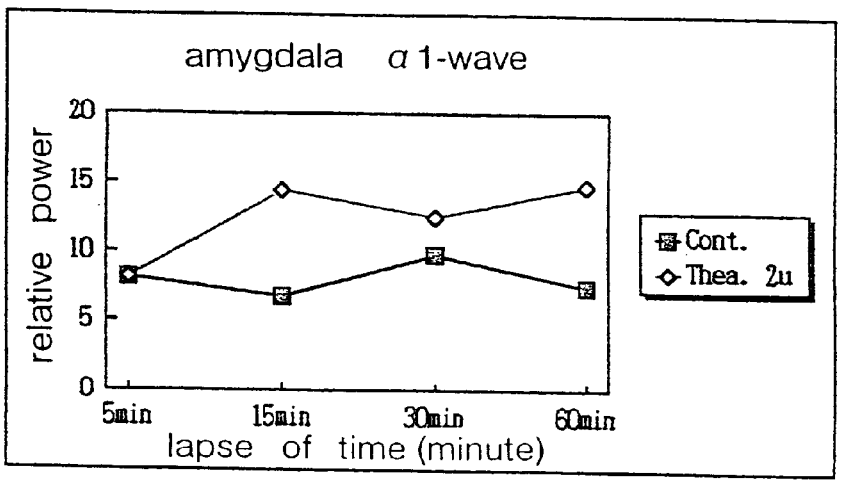
Figure 22A:
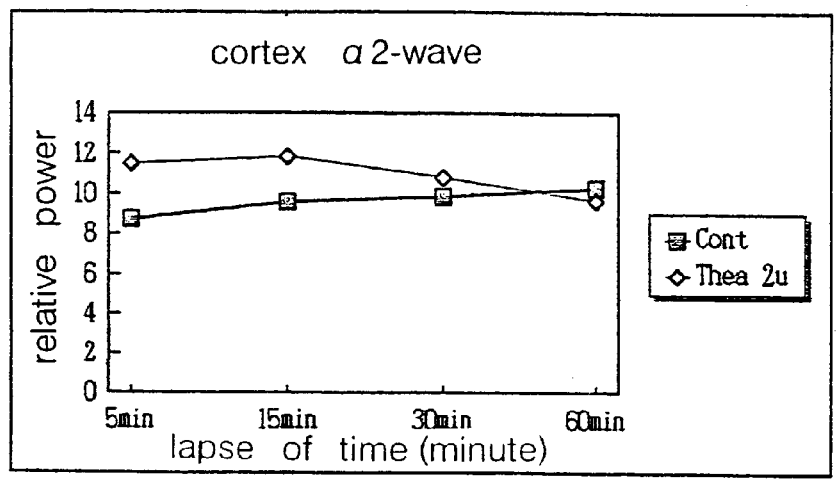
Figure 22B:
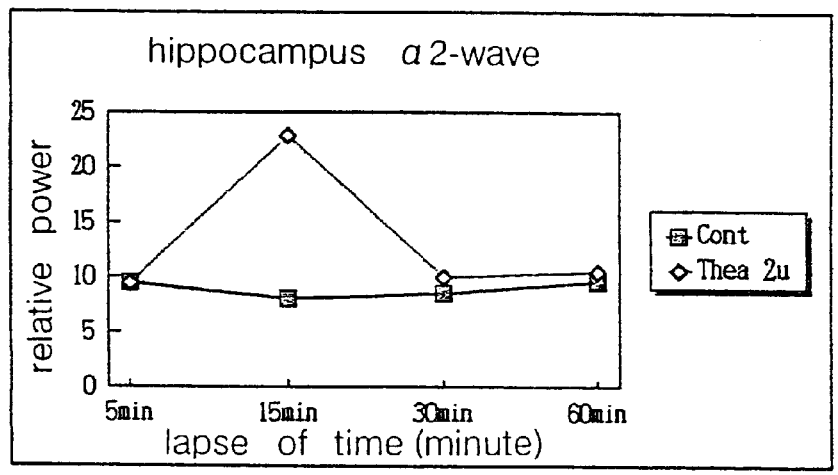
Figure 22C:
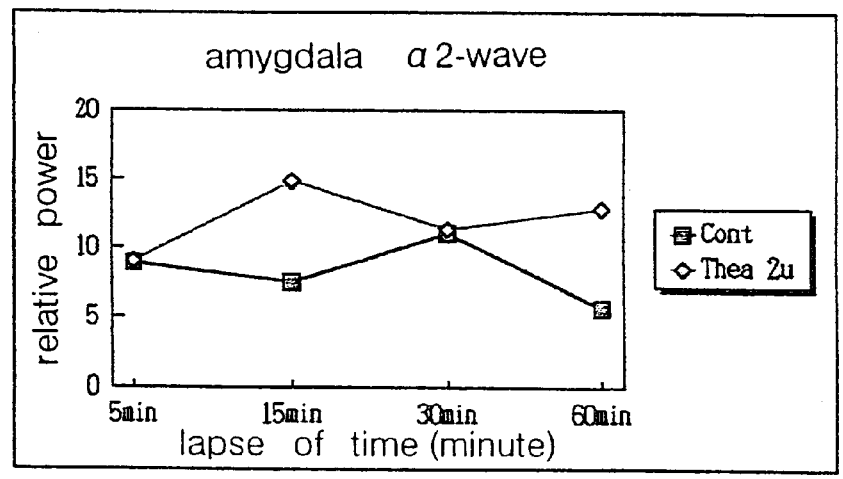
Figure 23A:
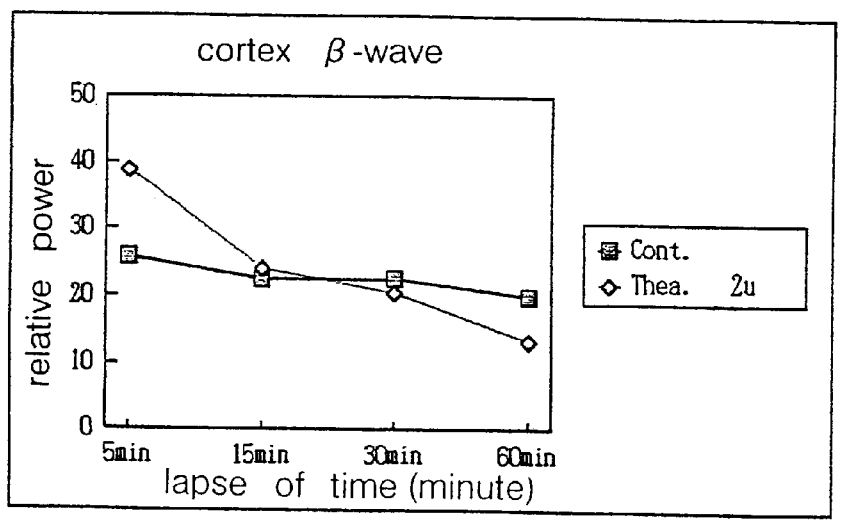
Figure 23B:
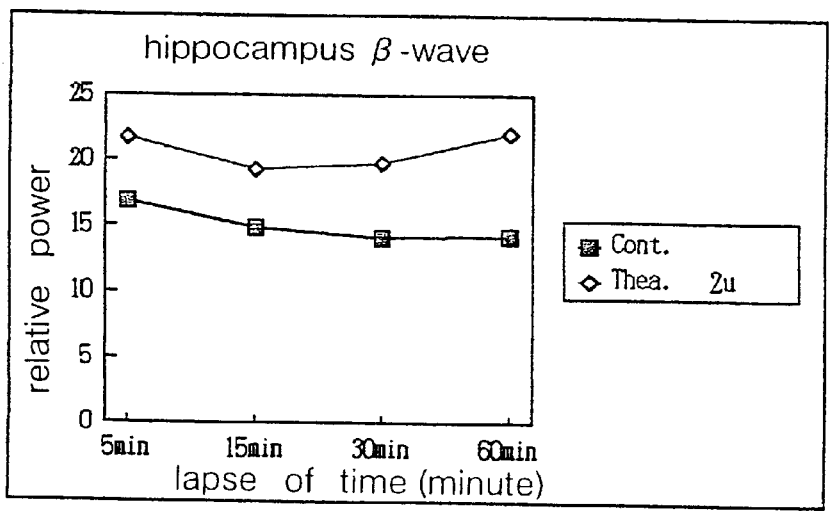
Figure 23C:
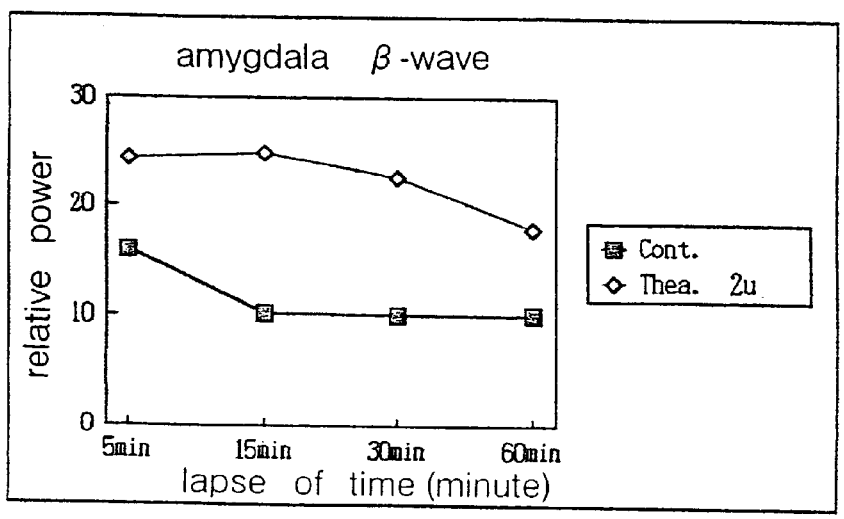

Measurement of $Ca^{2+}$ concentration in the neurons was carried out using a multi-point simultaneous observation device similarly to the above example 1. FIGS. 3 and 4 show the results.

[Experimental result]

Addition of theanine at both concentrations of 50 and 200 μM induced continuous changes in intracellular $Ca^{2+}$ concentration, which returned to the original level upon elimination of theanine.

Thus, it was demonstrated that a continuous administration of theanine at the minimum concentration of 50 μM or above would induce an increase in intracellular $Ca^{2+}$ concentration by direct action on neurons, cause plastic change in synapses and act effectively on memory and learning.

The point that there are active neurons with voluntary firing and inactive neurons and this experimental result have led to the following conclusions. Theanine when administered at the minimum concentration of 50 μM or higher would induce voluntary and periodic firing in the neurons which had been inactive until then synchronizing other active neurons. This voluntary firing ceased when theanine was washed out. It is comprehended that neurons would join synchronous firing of other neurons when they are stimulated by the effect of theanine but they secede from this firing activity when theanine is eliminated from their surroundings.

EXAMPLE 3

In this example, primary cultured rat cerebral cortical neurons were exposed to glutamic acid or a mixed solution of glutamic acid and theanine to examine antagonistic action of theanine to glutamate excitotoxicity by measuring the change in intracellular $Ca^{2+}$ concentration after a fixed period of time.

[Culture of rat cerebral cortical cells]

The same procedure as the above example 1 was carried out.

[Exposure to glutamic acid and theanine]

On the 15th day of culture, the above culture cells were exposed to solutions of 200 μM glutamic acid, 200 μM glutamic acid+20 μM theanine (commercial product; 99% purity), 200 μM glutamic acid+100 μM theanine, or 200 μM glutamic acid+1 mM theanine, respectively, for 16 hours. The neurons were washed by a salt solution once and then immersed in a salt solution for fura-2 uptake to measure intracellular $Ca^{2+}$ concentration. Untreated neurons were also prepared (control group) and $Ca^{2+}$ concentration in these cells was measured similarly.

Change in intracellular $Ca^{2+}$ concentration was measured by a multi-point simultaneous observation device developed by Kudo, et. al. in 1986 as in the above example 1. Table 1 shows the result.

TABLE 1

| Control | Glu | Glu + Theanine 20 μM | Glu + Theanine 100 μM | Glu + Theanine 1 μM |
|---------|-----|----------------------|-----------------------|---------------------|
| 100%    | 50% | 67%                  | 86%                   | 67%                 |

[Result]

In the control group, the intracellular $Ca^{2+}$ concentration changed in all the wells while the change was shown by only a half of the wells in the case of glutamic acid administration. In contrast, a simultaneous administration of glutamic acid and theanine resulted in the change in intracellular $Ca^{2+}$ concentration in more wells than those seen in the single administration of glutamic acid and, in particular, the ratio of the wells showing the change amounted to nearly 90% when the cells were exposed to a mixed solution of 200 μM glutamic acid and 100 μM theanine.

The above result demonstrated the inhibitory action of theanine on glutamate excitotoxicity.

EXAMPLE 4

In this example, primary cultured rat cerebral cortical neurons were exposed to glutamic acid or a mixture of glutamic acid and theanine for a fixed period of time. Glutamic acid was then eliminated from the neurons and the change in intracellular $Ca^{2+}$ concentration was measured with time to examine antagonistic action of theanine to the delayed neuronal death due to glutamate excitotoxicity.

[Culture of rat cerebral cortical cells]

The same procedure as the above example 1 was carried out.

[Exposure to glutamic acid and theanine]

The culture cells on the 7th day were exposed to the culture solution without any additive, 100 μM glutamic acid, 100 μM glutamic acid+100 μM theanine (commercial product; 99% purity), or 100 μM glutamic acid+1000 μM theanine, respectively, for 1 hour. After exposure, the cells were washed by the respective culture solutions twice and then returned to the culture solution. $Ca^{2+}$ concentrations in these cells were measured with time and the cultured neurons were immuno-histochemically stained at 1 week after the exposure to observe their states.

[Measurement of the change in $Ca^{2+}$ concentration in the neurons]

Similarly to the above example 1, the culture medium was changed to a salt solution for fura-2 uptake and the change in intracellular $Ca^{2+}$ concentration was measured using a multi-point simultaneous observation device developed by Kudo, et. al. in 1986. Table 2 below shows the result.

Unit in Table 2 is $\times 10^{-2}$ Hz.

TABLE 2

|                        |         | 0h      | 48h  | 120h |
|------------------------|---------|---------|------|------|
| Control                |         | 9.8     | 9.6  | 11.1 |
| Glu 100 μM             |         |         | 5.6  | 5.3  |
| Glu 100 μM + theanine  | 100 μM  |         | 4.2  | 3.1  |
| Glu 100 μM + theanine  | 1000 μM |         | 8.5  | 8.8  |

[Immunohistochemicalcal staining of neurons]

After fixation of the culture cells in 4% paraformaldehyde, the cell membrane was destructed by methanol acetate solution and non-specific binding sites were masked by 4% BSA.

To this preparation, a diluted primary antibody was added and incubated for 1–2 hours at 37° C. for reaction to take place. A diluted secondary antibody was then added in the same condition followed by addition of a fluorescent dye for reaction to take place. The preparation was covered with a mounting medium and dried at −4° C. in the dark. Microscopic photographs of each preparation (FIGS. 24–27) were then taken. Table 3 below shows the combination of antigen, antibody and fluorescent dye used in the experiment.

TABLE 3

| Antigen | Primary antibody | Secondary antibody | Fluorescent dye | Stained cells |
|---|---|---|---|---|
| MAP2 | Mouse monoclonal anti-MAP2 antibody | Biotinated anti-mouse anti body | Avidinated FITC/Texas red | Neurons |
| GFAP | Rabbit polyclonal anti-GFAP antibody | FITC/Texas red binding anti-rabbit antibody | | Glia cells |

[Result]

In the result in Table 2, frequency of the change in the $Ca^{2+}$ concentration in the neurons exposed to 100 μM glutamic acid continued to decrease with time even after washing but the decrease in the frequency of the $Ca^{2+}$ concentration change was inhibited markedly in the neurons exposed to 100 μM glutamic acid+1000 μM theanine.

Figure 24:
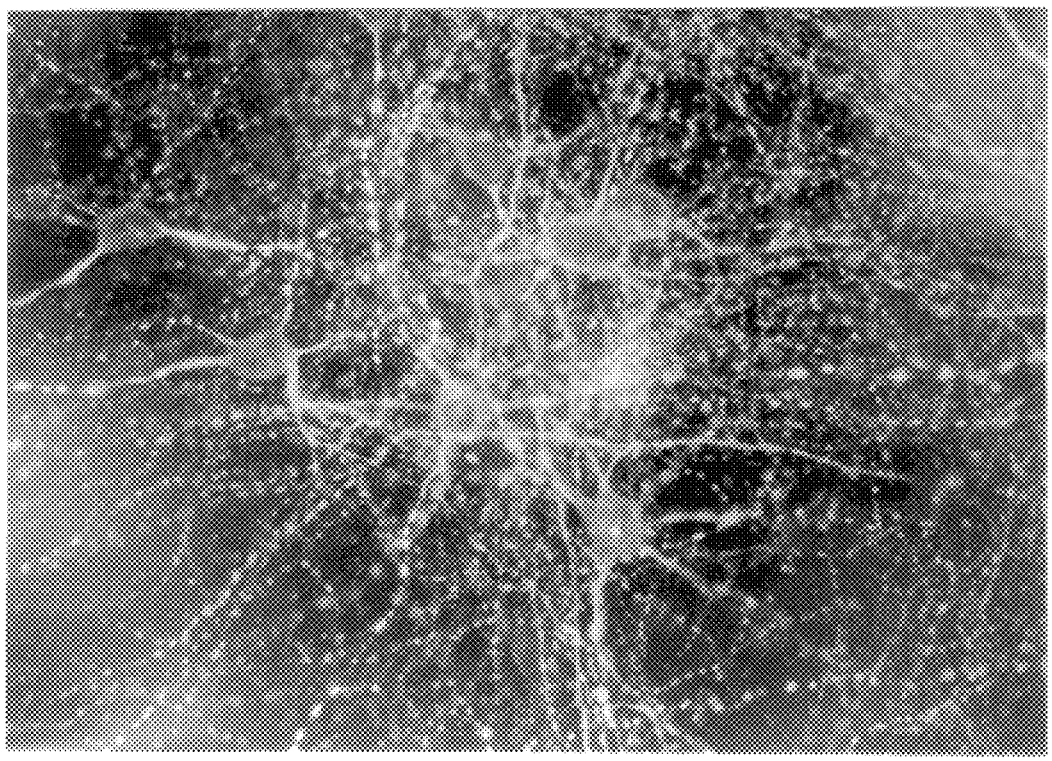
FIG. 24 shows the microscopic picture of neurons.
Figure 25:
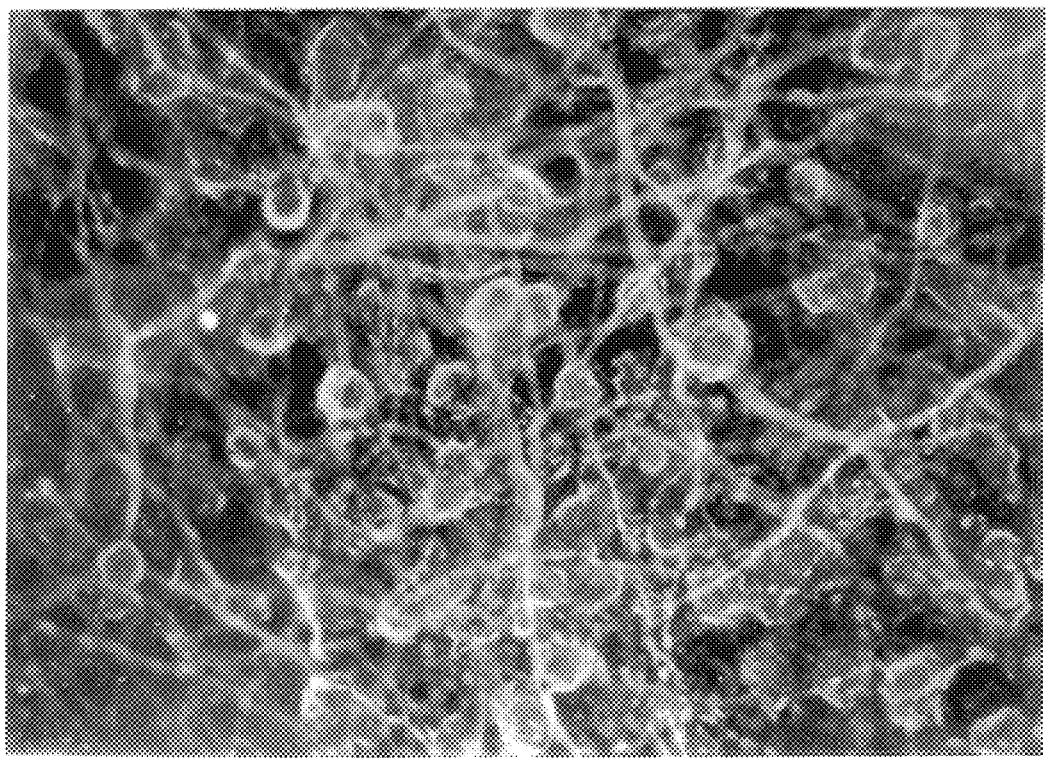
FIG. 25 shows the microscopic picture of neurons exposed to glutamic acid alone.
Figure 26:
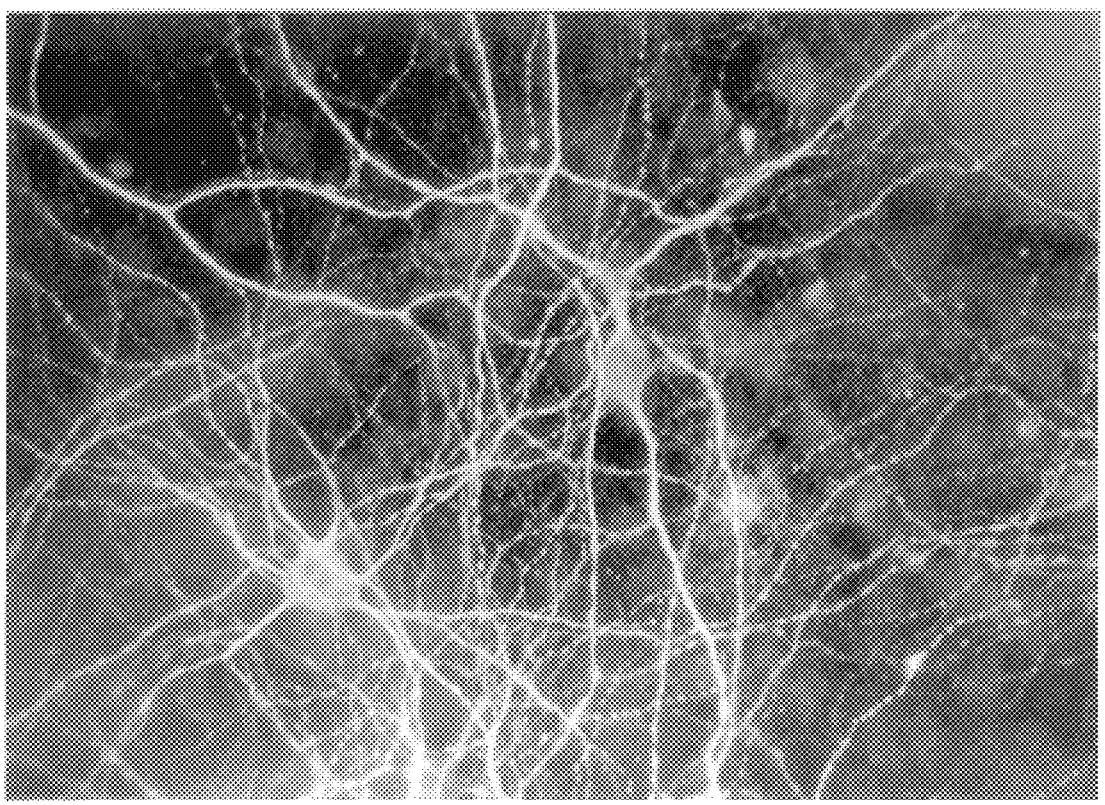
FIG. 26 shows the microscopic picture of neurons exposed to 100 μM glutamic acid and 100 μM theanine.
Figure 27:
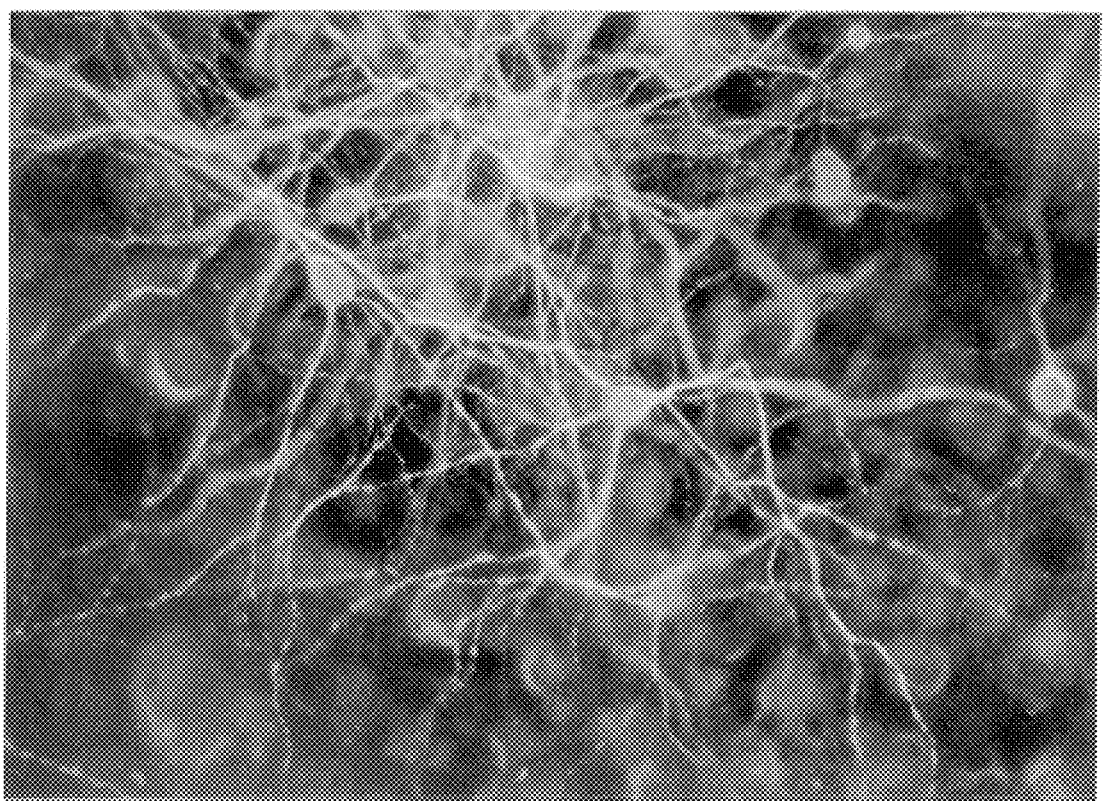
FIG. 27 shows the microscopic picture of neurons exposed to 100 μM glutamic acid and 100 μM theanine.

Microscopic photographs (FIGS. 24–27) confirmed that the neurons in the control group extended the dendrites well forming a neural circuit (FIG. 24). The cells exposed to glutamic acid alone had obscure outlines suggesting that they were damaged considerably (FIG. 25). In contrast, the neurons exposed to 100 μM glutamic acid+100 μM theanine were not damaged (FIG. 26). Moreover, the neurons exposed to 100 μM glutamic acid+1000 μM theanine extended dendrites well showing a good neural circuit formation (FIG. 27).

Although the frequency of change in $Ca^{2+}$ concentration in the neurons exposed to 100 μM glutamic acid+100 μM theanine decreased in the result shown in Table 2, FIG. 26 demonstrated that glutamate excitotoxicity was inhibited morphologically as mentioned above.

Thus, coexistance of theanine at the time of glutamic acid exposure can inhibit neurotoxicity of the acid at a concentration of 100 μM theanine against 100 μM glutamic acid. In other words, theanine has inhibitory effect on delayed glutamate excitotoxicity and can rescue neurons from the delayed cell death. Moreover, when 1000 μM theanine are added to 100 μM glutamic acid, the substance contributes to maintaining existence of neurons and glia cells in addition to the previously mentioned effects of repairing the damaged neural circuit to a normal one.

EXAMPLE 5

17 mg of theanine were dissolved in purified water or physiological salt solution for preparation of intravenous injection fluid in ampoule or vial so that a minimum dose of 0.17 mg/kg body weight was given even to a person weighing 100 kg.

EXAMPLE 6

Theanine was made into tablets or capsules by adding a granulating agent and a flavoring agent to contain an effective dose of the substance.

Here, granules were prepared according to the following prescription as an example.

10 g of the preparation contained:

| | |
|---|---|
| theanine | 100 mg |
| taurine | 100 mg |
| royal jelly | 20 mg |
| inositol | 5 mg |
| nicotinamide | 2 mg |
| vitamin B1 sulphate | 0.5 mg |
| vitamin B2 phosphoric ester | 0.5 mg |
| vitamin B6 | 0.5 mg |
| anhydrous caffeine | 5 mg |
| granulating agent | appropriate quantities |
| flavoring agent | appropriate quantities |

Another example of prescription is as follows.

10 g of the preparation contained:

| | |
|---|---|
| theanine | 100 mg |
| taurine | 100 mg |
| royal jelly | 20 mg |
| inositol | 5 mg |
| nicotinamide | 2 mg |
| vitamin B1 sulphate | 0.5 mg |
| vitamin B2 phosphoric ester | 0.5 mg |
| vitamin B6 | 0.5 mg |
| granulating agent | appropriate quantities |
| flavoring agent | appropriate quantities |

EXAMPLE 7

A drink was prepared by the following prescription.

100 ml of the preparation contained:

| | |
|---|---|
| theanine | 1000 mg (57.4 mM concentration) |
| taurine | 1000 mg |
| royal jelly | 200 mg |
| inositol | 50 mg |
| nicotinamide | 20 mg |
| vitamin B1 sulphate | 5 mg |
| vitamin B2 phosphoric ester | 5 mg |
| vitamin B6 | 5 mg |
| anhydrous caffeine | 50 mg |

EXAMPLE 8

Food or canned drink was prepared according to the following prescription.

200 ml of the preparation contained:

| | |
|---|---|
| theanine | 1000 mg (28.7 mM concentration) |
| fructose/glucose | 30000 mg |
| citric acid | 200 mg |
| royal jelly | 200 mg |
| sodium L-aspartate | 200 mg |
| inositol | 50 mg |
| nicotinamide | 20 mg |
| vitamin C | 70 mg |
| vitamin B1 sulphate | 5 mg |
| vitamin B2 phosphoric ester | 5 mg |
| vitamin B6 | 5 mg |
| anhydrous caffeine | 50 mg |
| sweetening agent | appropriate amount |
| granulating agent or water | appropriate amount |

REFERENCE EXAMPLE

Theanine was administered to rats at various doses and brain waves were observed after the administration to examine the minimum effective dose of the substance to brain neurons.

1. Test animals and group composition

After 1-week preliminary breeding of 9-week-old male Wister/st rats (weighing 260–320 g), electrode implantation was performed under NEMBUTAL anesthesia to fix stainless-steel screw electrodes in the right and left frontal regions and implant stainless-steel parallel dipolar electrodes in the hippocampus and amygdala. Intramuscular injection of cefmetazone was given for 4 days after the surgery for prevention of infection. Preliminary test was conducted three times on and after 10 days of the surgery to select the rats with stable brain waves as the subjects, which were allocated to 5 groups from A to E each consisting of 6 animals.

2. Preparation and administration of test substance

Anhydrous theanine was dissolved in a physiological salt solution to prepare physiological salt solutions of theanine at the following doses. The substance was administered intravenously into the caudal vein.

Theanine doses
Group A: 0 μmol theanine/kg body weight
Group B: 1 μmol theanine/kg body weight
Group C: 2 μmol theanine/kg body weight
Group D: 5 μmol theanine/kg body weight
Group E: 10 μmol theanine/kg body weight 3. Measurement of brain waves Brain waves were measured by the bipolar leading and the detected brain waves were subjected to filtering through a high-frequency blocking filter of 50-Hz blocking wavelength and 24 db/oct reduction specificity and recorded on a photomagnetic disc at 200-Hz sampling frequency by a digital recorder (TEAC: DR-M2a). Power spectrum of the recorded brain waves was determined later by fast Fourier transformation using a personal computer (Nippon Denki: PC-9801BA) and a wave analysis software (Development Corporation: DADISP Work-sheet) and relative powers of δ-, θ-, α1-, α2- and β-waves were calculated. Brain waves were measured at 5, 15, 30 and 60 minutes after theanine administration for 3 minutes/session and spectrum was smoothed by adding 5 measurements in 5-second intervals showing less artifact.

Generally speaking, α-wave appears at the resting time with the eyes closed, β-wave appears during active state of the brain, δ-wave during a sound sleep and θ-wave during a doze.

4. Experimental result

FIGS. 5–13 show the relative powers of δ-, θ-, α1-, α2- and β-waves in the cortex, hippocampus and amygdala of the animals in the respective groups shown above at 15, 30 and 60 minutes after theanine administration.

It was shown that the relative power of δ-wave appearing during sleep was suppressed in the cortex, hippocampus and amygdala in Groups B (given 1 μmol/kg body weight), C (given 2 μmol/kg body weight) and D (given 5 μmol/kg body weight) while the relative power of β-wave appearing during activity increased; the rate of increase was particularly remarkable in Group C (given 2 μmol/kg body weight).

FIGS. 14–18 show the time-series changes of the relative powers of δ-, θ-, α1-, α2- and β-waves in the respective sites in Group B while FIGS. 19–23 show those in Group C.

It was demonstrated that the relative power of δ-wave appearing during sleep was suppressed in the cortex, hippocampus and amygdala in Groups B (given 1 μmol/kg body weight) and C (given 2 μmol/body weight).

Moreover, the relative power of β-wave appearing during activity increased remarkably in the hippocampus and amygdala in Groups B (given 1 μmol/kg body weight) and C (given 2 μmol/kg body weight) and the rate of increase was particularly distinct in Group C (2 μmol/kg body weight).

Thus, it was confirmed that theanine administered intravenously at a minimum dose of 1 μmol/kg body weight would act on the brain neurons effectively.

What is claimed is:

1. A method for preventing or treating Parkinson's disease comprising administering to a person in need thereof an effective amount of a composition comprising theanine.

2. The method according to claim 1 wherein theanine is dissolved in a physiological salt solution or glucose solution for intravenous injection and is administered at a dose of 0.17 mg/kg body weight or higher.

3. A method for preventing or treating traumatic nervous disorder comprising administering to a person in need thereof an effective amount of a composition comprising theanine.

4. A method for treating and preventing glutamic-acid induced brain disorder comprising administering to a person in need thereof an effective amount of a composition comprising theanine.

5. A method for preventing or treating brain apoplexy comprising administering to a person in need thereof an effective amount of a composition comprising theanine.

6. A method for preventing or treating cerebral ischemia accompanying brain surgery comprising administering to a person in need thereof an effective amount of a composition comprising theanine.

7. The method according to claim 3, wherein theanine is dissolved in a physiological salt solution or glucose solution for intravenous injection and is administered at a dose of 0.17 mg/kg body weight or higher.

8. The method according to claim 4, wherein theanine is dissolved in a physiological salt solution or glucose solution for intravenous injection and is administered at a dose of 0.17 mg/kg body weight or higher.

9. The method according to claim 5, wherein theanine is dissolved in a physiological salt solution or glucose solution for intravenous injection and is administered at a dose of 0.17 mg/kg body weight or higher.

10. The method according to claim 6, wherein theanine is dissolved in a physiological salt solution or glucose solution for intravenous injection and is administered at a dose of 0.17 mg/kg body weight or higher.

* * * * *